United States Patent
Jaquish et al.

(10) Patent No.: US 12,017,118 B2
(45) Date of Patent: Jun. 25, 2024

(54) SYSTEMS, METHODS AND DEVICES FOR DISPLAYING EXERCISE INFORMATION

(71) Applicant: Jaquish Biomedical Corporation, Nevada City, CA (US)

(72) Inventors: John Paul Jaquish, Nevada City, CA (US); Paul Edward Jaquish, Nevada City, CA (US); Henry David Alkire, Nevada City, CA (US)

(73) Assignee: Jaquish Biomedical Corporation, Nevada City, CA (US)

( * ) Notice: Subject to any disclaimer, the term of this patent is extended or adjusted under 35 U.S.C. 154(b) by 0 days.

(21) Appl. No.: 17/959,101

(22) Filed: Oct. 3, 2022

(65) Prior Publication Data
US 2023/0106092 A1   Apr. 6, 2023

Related U.S. Application Data

(60) Provisional application No. 63/252,965, filed on Oct. 6, 2021.

(51) Int. Cl.
*A63B 24/00* (2006.01)
*A63B 21/00* (2006.01)
(Continued)

(52) U.S. Cl.
CPC ...... *A63B 24/0062* (2013.01); *A63B 21/0442* (2013.01); *A63B 21/4035* (2015.10);
(Continued)

(58) Field of Classification Search
CPC ............ A63B 24/0062; A63B 21/4035; A63B 2071/065; A63B 2220/58; A63B 2220/833; A63B 21/02; A63B 21/407; A63B 21/00
See application file for complete search history.

(56) References Cited

U.S. PATENT DOCUMENTS 1,019,861 A   3/1912   Titus
1,997,139 A   4/1935   Lawrence
(Continued)

FOREIGN PATENT DOCUMENTS

CN   107019888 A * 8/2017 ......... A63B 24/0003
DE   20 2008 00763 U1   3/2008
(Continued)

OTHER PUBLICATIONS

GoFit bar, announced 2016 [online], [site visited May 3, 2021]. Available on internet:https://www.amazon.com/Go Fit-RAB-Resistance-Traini ng-Bar/dp/B01MTM7 N 97/ref=sr 131?dchild=I &keywords=exercise+bar+with+hook&qid=1619657583&s=sporting-goods&sr=1-31 (Year: 2016).

(Continued)

*Primary Examiner* — Megan Anderson
*Assistant Examiner* — Jacqueline N L Loberiza
(74) *Attorney, Agent, or Firm* — MORGAN, LEWIS & BOCKIUS LLP

(57) ABSTRACT

An exercise bar is provided. The exercise bar includes a handle tube with a longitudinal interior bore. The handle tube has a first end and a second end. A center shaft has an outer surface. The center shaft is fitted through the longitudinal interior bore exposing a first end portion of the center shaft at the first end of the handle tube and exposing a second end portion of the center shaft at the second end of the handle tube. A sensor is disposed on a mounting section of the outer surface of the center shaft between the first and second portion of the center shaft. A processor is disposed in an interior of the exercise bar. The sensor is in electronic communication with the processor in the exercise bar.

18 Claims, 21 Drawing Sheets

(51) Int. Cl.
  *A63B 21/04* (2006.01)
  *A63B 21/055* (2006.01)
  *A63B 23/035* (2006.01)
  *A63B 23/12* (2006.01)
  *A63B 71/06* (2006.01)
  *G16H 20/30* (2018.01)

(52) U.S. Cl.
  CPC .... *A63B 21/4043* (2015.10); *A63B 23/03525* (2013.01); *A63B 23/1209* (2013.01); *G16H 20/30* (2018.01); *A63B 21/0552* (2013.01); *A63B 2071/0625* (2013.01); *A63B 2071/065* (2013.01); *A63B 2071/068* (2013.01); *A63B 2071/0683* (2013.01); *A63B 2220/58* (2013.01); *A63B 2220/833* (2013.01); *A63B 2225/20* (2013.01); *A63B 2225/50* (2013.01)

(56) References Cited

U.S. PATENT DOCUMENTS

| Number | Type | Date | Name | Notes |
|---|---|---|---|---|
| 2,470,815 | A | 5/1949 | Roosevelt | |
| 2,637,555 | A | 5/1953 | Klaudt | |
| 3,117,781 | A | 1/1964 | Vargo | |
| 3,193,288 | A | 7/1965 | Vell | |
| 3,215,429 | A | 11/1965 | Shaboo | |
| 3,256,015 | A | 6/1966 | Perrin | |
| 3,785,644 | A | 1/1974 | Bradley | |
| 3,910,573 | A | 10/1975 | Jamba | |
| 4,200,281 | A | 4/1980 | Wang | |
| 4,257,592 | A | 3/1981 | Jones | |
| 4,441,707 | A | 4/1984 | Bosch | |
| D274,829 | S | 7/1984 | Bankier | |
| 4,518,162 | A | 5/1985 | Oates | |
| 4,770,414 | A | 9/1988 | Fredrickson | |
| 4,893,810 | A | 1/1990 | Lee | |
| 5,112,287 | A | 5/1992 | Brewer | |
| 5,125,649 | A | 6/1992 | Fuller | |
| 5,178,596 | A | 1/1993 | McIntire | |
| 5,197,934 | A | 3/1993 | Wirtz | |
| D353,419 | S | 12/1994 | Sprague | |
| 5,514,058 | A | 5/1996 | Buoni | |
| 5,540,642 | A | 7/1996 | Sprague | |
| 5,645,511 | A | 7/1997 | Le Roux | |
| 5,653,665 | A | 8/1997 | Neeley | |
| 5,746,687 | A | 5/1998 | Vial | |
| 5,776,041 | A | 7/1998 | Fisher | |
| 5,830,110 | A | 11/1998 | Fielding | |
| 5,885,196 | A | 3/1999 | Gvoich | |
| 5,904,640 | A | 5/1999 | Shahinian | |
| 6,203,476 | B1 | 3/2001 | Wang et al. | |
| 6,280,366 | B1 | 8/2001 | Hsieh | |
| D474,818 | S | 5/2003 | Yu | |
| D482,748 | S | 11/2003 | Flynt | |
| 7,052,449 | B2 | 5/2006 | Chen | |
| D526,367 | S | 8/2006 | Loccarini | |
| 7,090,627 | B1 | 8/2006 | Walker | |
| 7,175,574 | B2 | 2/2007 | Carmel et al. | |
| 7,387,599 | B1 | 6/2008 | Hsu | |
| 7,465,259 | B2 | 12/2008 | Mok | |
| D590,457 | S | 4/2009 | Mishan | |
| 7,578,775 | B2 | 8/2009 | Terry | |
| 7,601,101 | B2 | 10/2009 | Jackson | |
| D604,374 | S | 11/2009 | Bizzell | |
| D633,155 | S | 2/2011 | Brun | |
| 7,892,158 | B2 | 2/2011 | Varga | |
| 7,922,624 | B1 | 4/2011 | Fairhurst | |
| 8,025,615 | B1 | 9/2011 | Sargent | |
| 8,033,964 | B1 | 10/2011 | Chen | |
| D655,356 | S | 3/2012 | Sandman | |
| 8,142,335 | B1 | 3/2012 | Leach | |
| D682,374 | S | 5/2013 | Wilkinson | |
| D724,163 | S | 3/2015 | Kelley | |
| D739,481 | S | 9/2015 | Glickfield | |
| 9,180,335 | B1 | 11/2015 | Wu | |
| D748,745 | S | 2/2016 | Hansen | |
| 9,254,405 | B1 | 2/2016 | Marji | |
| D778,374 | S | 2/2017 | Jaquish | |
| 9,675,837 | B2 | 6/2017 | Smith | |
| 9,724,553 | B2 | 8/2017 | Kaye | |
| D798,396 | S | 9/2017 | Agate | |
| 9,789,360 | B1* | 10/2017 | Schaffer | A63B 71/0622 |
| D802,153 | S | 11/2017 | Kelly | |
| 9,844,696 | B2 | 12/2017 | Anderson | |
| 9,907,993 | B2 | 3/2018 | Penney | |
| 9,919,176 | B2 | 3/2018 | Christie et al. | |
| 9,925,410 | B2 | 3/2018 | Duffy | |
| 10,188,173 | B1* | 1/2019 | Walsh | A43B 3/246 |
| D842,940 | S | 3/2019 | Harden | |
| D849,857 | S | 5/2019 | Tartell | |
| D854,635 | S | 7/2019 | Dunahay | |
| D865,084 | S | 10/2019 | Croxton | |
| D895,033 | S | 9/2020 | Jaquish | |
| D895,739 | S | 9/2020 | Jaquish | |
| D898,132 | S | 10/2020 | Jaquish | |
| D898,133 | S | 10/2020 | Jaquish | |
| D902,329 | S | 11/2020 | Jaquish | |
| D902,330 | S | 11/2020 | Jaquish | |
| D902,834 | S | 11/2020 | Kern | |
| D910,124 | S | 2/2021 | Jaquish | |
| D937,369 | S | 11/2021 | Jaquish | |
| D954,858 | S | 6/2022 | Karvandi | |
| 11,383,120 | B2 | 7/2022 | Cone | |
| 2002/0123416 | A1 | 9/2002 | Huang | |
| 2002/0137609 | A1 | 9/2002 | Rosati | |
| 2002/0198081 | A1 | 12/2002 | Chen | |
| 2003/0096680 | A1 | 5/2003 | Nethery | |
| 2005/0113218 | A1 | 5/2005 | Sewitch | |
| 2005/0113221 | A1 | 5/2005 | Dovner | |
| 2005/0113222 | A1* | 5/2005 | Dovner | A63B 21/00043 482/121 |
| 2005/0233877 | A1 | 10/2005 | Lin | |
| 2005/0239617 | A1 | 10/2005 | Tenaglia | |
| 2005/0245370 | A1 | 11/2005 | Boland | |
| 2006/0019806 | A1 | 1/2006 | Mikulski | |
| 2006/0276314 | A1 | 12/2006 | Wilson | |
| 2007/0197352 | A1 | 8/2007 | Charniga | |
| 2007/0207905 | A1 | 9/2007 | Winston | |
| 2008/0081747 | A1 | 4/2008 | Mok | |
| 2008/0242438 | A1 | 10/2008 | Sato | |
| 2008/0287272 | A1* | 11/2008 | Luckadue | A63B 21/0552 482/107 |
| 2009/0192022 | A1 | 7/2009 | Kulka | |
| 2010/0152002 | A1 | 6/2010 | Knight | |
| 2010/0173760 | A1 | 7/2010 | Hall | |
| 2010/0317496 | A1 | 12/2010 | Abranchess | |
| 2010/0319814 | A1 | 12/2010 | Perez et al. | |
| 2011/0251033 | A1 | 10/2011 | Blancher | |
| 2012/0094812 | A1 | 4/2012 | Smiley | |
| 2012/0225758 | A1 | 9/2012 | Shaw | |
| 2013/0172155 | A1* | 7/2013 | Adamchick | A63B 21/4043 482/8 |
| 2013/0310233 | A1 | 11/2013 | Dahlquist | |
| 2014/0087927 | A1 | 3/2014 | Richard | |
| 2014/0155232 | A1 | 6/2014 | Wolan | |
| 2014/0287889 | A1 | 9/2014 | Grace | |
| 2014/0295983 | A1 | 10/2014 | Nooner | |
| 2014/0302968 | A1 | 10/2014 | Velikin | |
| 2014/0336019 | A1 | 11/2014 | Villella | |
| 2014/0349821 | A1 | 11/2014 | Davis | |
| 2015/0126342 | A1 | 5/2015 | Kaye | |
| 2015/0190679 | A1 | 7/2015 | Carbone | |
| 2016/0038781 | A1 | 2/2016 | Christie | |
| 2016/0144217 | A1 | 5/2016 | Oltorik, Jr. | |
| 2016/0144221 | A1 | 5/2016 | Wallander | |
| 2016/0287929 | A1 | 10/2016 | Poole | |
| 2017/0188649 | A1 | 7/2017 | Allen | |
| 2017/0209730 | A1 | 7/2017 | Sise | |
| 2017/0216650 | A1 | 8/2017 | Simmons | |
| 2017/0266486 | A1 | 9/2017 | Anderson | |
| 2017/0274239 | A1 | 9/2017 | Barella | |
| 2018/0036580 | A1 | 2/2018 | Hao | |
| 2018/0104538 | A1 | 4/2018 | Uygan | |
| 2018/0161619 | A1 | 6/2018 | Rossi | |

(56) References Cited

U.S. PATENT DOCUMENTS

| | | |
|---|---|---|
| 2018/0236295 A1 | 8/2018 | Oltorik |
| 2018/0236299 A1 | 8/2018 | Warriner |
| 2018/0326245 A1 | 11/2018 | Davis |
| 2019/0329084 A1 | 10/2019 | Stewart |
| 2020/0054917 A1 | 2/2020 | Lin |
| 2020/0269080 A1* | 8/2020 | Jaquish .............. A63B 21/0428 |
| 2020/0289890 A1* | 9/2020 | Kim ....................... G01C 19/00 |
| 2021/0128971 A1 | 5/2021 | Orfield |

FOREIGN PATENT DOCUMENTS

| | | | |
|---|---|---|---|
| WO | WO 2017/095990 A2 | 6/2017 | |
| WO | WO-2017095990 A2 * | 6/2017 | ......... A63B 21/0004 |

OTHER PUBLICATIONS

X3 Bar Review—Portable, Heavy-Resistance Band Training on the road or at home—Youtube (https://www.youtube.com/watch?v=ikYqDtFxPfc) (Year: 2018).
STIC search report (Year: 2023).
Google search (Year: 2023).
Youtube search (Year: 2023).
Facebook search (Year: 2023).

* cited by examiner

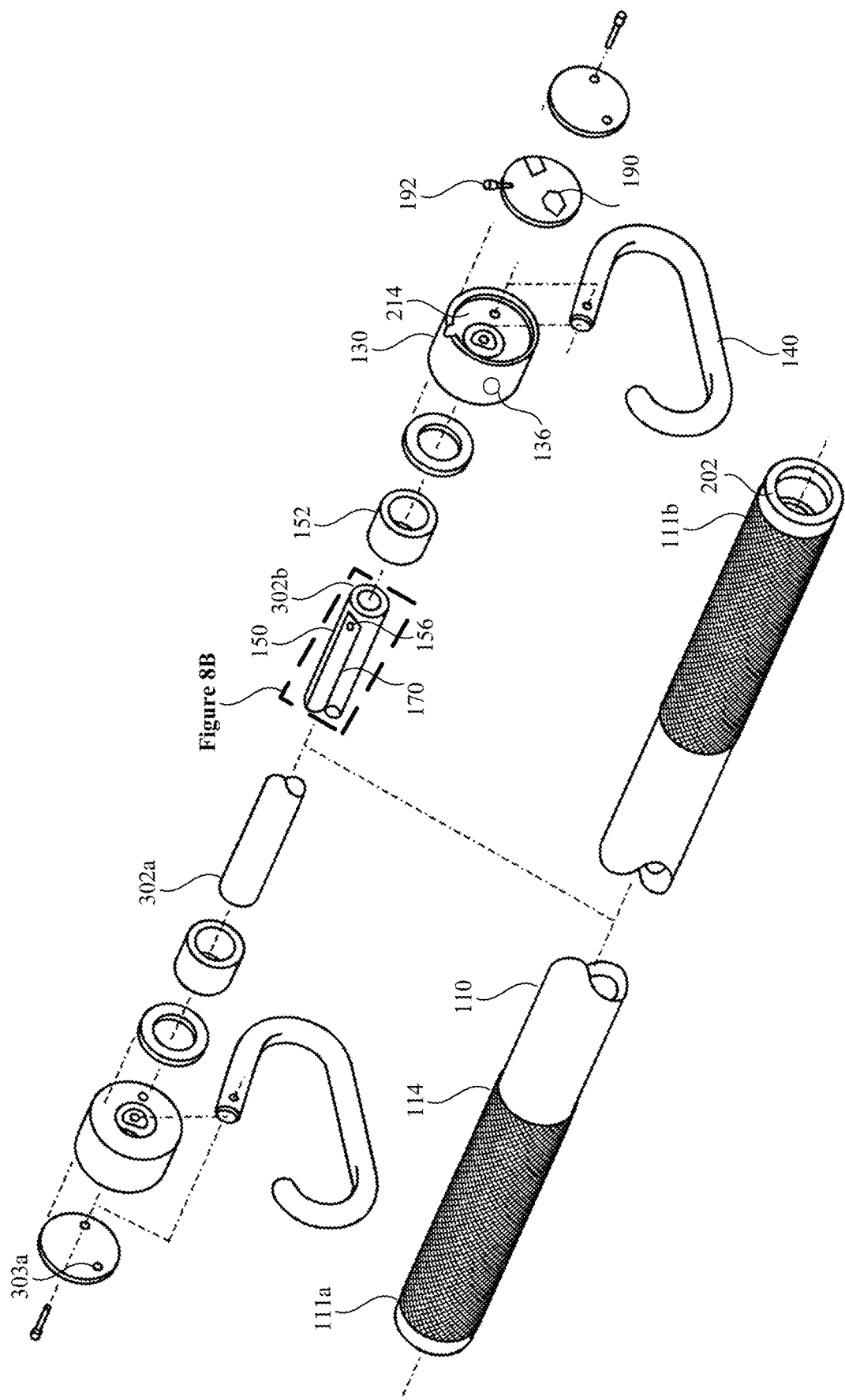

1100

(1102) A method for providing sensory feedback at an exercise bar.

(1104) Offset a longitudinal axis of a center shaft of the exercise bar.

(1106) Determining, when offsetting of the longitudinal axis of the center shaft, by a processor in electronic communication with a sensor coupled to the center shaft, an amount of a strain on the exercise bar when offsetting the longitudinal axis of the center shaft.

(1108) Communicating, by the processor, one or more instructions for causing a controller to change a respective state of a sensory output mechanism based on the determined amount of the strain. The one or more instructions is configured to cause a user operating the exercise bar to sense the change in the respective state of the sensory output mechanism.

(1110) Repeating the offsetting the longitudinal axis of the center shaft, the determining the amount of the strain, and the communicating one or more instructions, and dynamically updating a digital representation responsive to the repeating.

*(1202)* A method for displaying exercise data at a computer system. The computer system includes a display, one or more processors, and a memory storing at least one program for execution by the one or more processors. The at least one program includes instructions performing the method.

*(1204)* Receiving, in electronic format, from an exercise bar, a plurality of data elements captured, at least in part, when offsetting a longitudinal axis of the exercise bar.

*(1206)* Generating, by one or more models, from a set of data elements in the plurality of data elements, a digital representation of the set of data elements.

*(1208)* Displaying, on the display, the digital representation of the set of data elements. The display of the digital representation includes a chart. The chart includes a plurality of nodes at least one edge connecting a respective node in the plurality of nodes to at least one other node. Each respective node in the plurality of nodes represents a corresponding data element in the set of data elements.

*(1210)* Repeating the receiving the plurality of data elements, the generating the digital representation, and the displaying the digital representation, and dynamically updating a digital representation responsive to the repeating.

*(1212)* Communicating, in electronic format, the one or more instructions for firing a first configuration to the exercise bar.

Figure 12

SYSTEMS, METHODS AND DEVICES FOR DISPLAYING EXERCISE INFORMATION

CROSS REFERENCE TO RELATED APPLICATIONS

The Present Application claims priority to U.S. Provisional Patent Application No. 63/252,965, entitled, "Systems, Methods, and Devices for Displaying Exercise Information," filed on Oct. 6, 2021, which is hereby incorporated by reference in their entireties for all purposes.

FIELD

The present disclosure relates generally to exercise apparatuses and exercise regimens. More particularly, the present disclosure pertains to an improved exercise apparatus that allows for determining an amount of a strain on the exercise apparatus while the exercise apparatus is in use.

BACKGROUND

Standard exercise devices, such as Olympic bars, allow a user to perform various exercises with free weights or variable resistance exercise bands. Conventional exercise regimens solutions seek to either improve the mechanical functionality of exercise devices or make use of in-person training coaches. However, these conventional exercise regimen solutions provide unsatisfactory stand-alone feedback to the exerciser in real time while the exerciser is performing exercises.

Given the above disclosure, what is needed in the art are improved exercise devices that allow for sensory feedback and/or display of exercise information captured at an exercise device.

SUMMARY

The present disclosure addresses the above-identified shortcomings by providing improved exercise devices and methods of using such improved exercise devices. The improved variable resistance exercise devices are more stable than the above-identified prior art variable resistance exercise devices while at the same time offering the same advantages over conventional constant resistance exercise devices such as free weights.

An aspect of the present disclosure is directed to providing an improved exercise bar that captures exercise information using a sensor housed by the exercise bar. Specifically, the sensor is configured to determine an amount of strain that is applied to the exercise bar, such as a maximum force experienced by the exercise bar when an end-user performs an exercise with it. Furthermore, in some embodiments, the exercise bar of the present disclosure utilizes wireless communication techniques to communicate with a remote client device through a communication network. From this, the client device receives the exercise information of the sensor transmitted from the exercise bar and displays, by way of a client application, a digital representation of the exercise information of the sensor so as to provide benefit and instruction to the end-user.

In some embodiments, the exercise bar communicates with the client device, exercise information about real time loading force being experienced by a user and, therefore, the exercise bar, during the course of an exercise with the exercise bar. Accordingly, the systems and methods of the present disclosure utilize this exercise information, such as by outputting numerical and/or graphical feedback in the form of a digital representation of the exercise information regarding exercise performance. In this way, the feedback can be reviewed by the end-user in real time during performance of the exercise or at a later date. In some embodiments, the systems and methods of the present disclosure utilize the exercise information to detect if one or more threshold conditions is satisfied by the exercise bar on a continuous basis throughout the performance of the exercise. In some embodiments, the systems and methods of the present disclosure utilize the exercise information to display a digital representation of the exercise information, such as by displaying numerical or graphical representations of the exercise information juxtaposed with digital representations of exercise information from previous workouts performed with the exercise bar.

In some embodiments, the systems and methods of the present disclosure utilize the exercise information to display historical exercise information. In some embodiments, the systems and methods of the present disclosure utilize the exercise information to display quantitative exercise performance measurements including a maximum strain applied to an exercise bar, a repetition count when performing a respective exercise, a period of time the exercise bar has an applied strain, a period of time of a phase of the respective exercise (e.g., eccentric phase and/or concentric phase), or a combination thereof.

In some embodiments, the systems and methods of the present disclosure provide one or more recommendations for an end-user that are generated based on exercise history of the end-user, such as how the end-user can improve a quality of performance of exercises with the exercise bar in the future.

In some embodiments, the systems and methods of the present disclosure provide a client application for presenting exercise information. In some embodiments, the systems and methods of the present disclosure allow the end-user, by way of the client application, to review exercise historical data or digital representations of exercise data collected by an exercise bar. In some embodiments, the systems and methods of the present disclosure allow the end-user to review exercise data associated with a corresponding user profile of the end-user. In some embodiments, the systems and methods of the present disclosure allow for the communication and sharing of the exercise information created by both a first user and a second user, or combining the exercise information from any number of users, so as to create a competitive experience, leader board, or simulated group workout.

Turning to more specific aspects of the present disclosure, in accordance with some embodiments, an exercise bar is provided. The exercise bar includes a handle tube with a longitudinal interior bore. The handle tube includes a first end and a second end. A center shaft of the exercise bar includes an outer surface. The center shaft is fitted through the longitudinal interior bore, which exposes a first end portion of the center shaft at the first end of the handle tube and a second end portion of the center shaft at the second end of the handle tube. The exercise bar includes a sensor disposed on a mounting section of the outer surface of the center shaft between the first and second portion of the center shaft. Furthermore, the exercise bar includes a processor disposed in an interior of the exercise bar. The sensor is in electronic communication with the processor in the exercise bar.

In some embodiments, the center shaft is a hollow center shaft.

In some embodiments, the mounting section includes a lateral bore, which exposes an interior of the hollow center shaft for physical electronic communication between the sensor and the processor.

In some embodiments, the exercise bar further includes a switch mechanism interposed between the sensor and the processor. The switch mechanism is configured to interrupt the electronic communication.

In some embodiments, the mounting section is at a midpoint of the center shaft.

In some embodiments, the handle tube further includes a first circumferential grip region on an exterior circumferential surface of the handle tube.

In some embodiments, the first circumferential grip region includes a midpoint of the exterior circumferential surface of the handle tube.

In some embodiments, the center shaft longitudinally rotates independent of the handle tube.

In some embodiments, the sensor includes a strain sensor.

In some embodiments, the sensor includes a Wheatstone bridge sensor, such as a balanced Wheatstone bridge sensor or a full Wheatstone bridge sensor.

In some embodiments, a first longitudinal axis of the center shaft is parallel to a second longitudinal axis of the sensor.

In some embodiments, the first longitudinal axis of the center shaft and a third longitudinal axis of the handle tube interact along a length of the exercise bar.

In some embodiments, the exercise bar further includes a first end cap fixedly disposed about the first end of the handle tube or the first end portion of the center shaft.

In some embodiments, an interior portion of the first end cap is configured to accommodate the processor.

In some embodiments, the first end cap is fixedly disposed about the first end portion of the center shaft. In such embodiments, the first end cap longitudinally rotates independent of the handle tube.

In some embodiments, the exercise bar further includes a second end cap fixedly disposed about the second end of the handle tube or the second end portion of the center shaft.

In some embodiments, the second end cap is configured to accommodate a battery configured to provide power to at least the processor.

In some embodiments, an exterior circumferential surface of the first end cap includes a first bore configured to accommodate a light source in electronic communication with the processor.

In some embodiments, the exterior circumferential surface of the handle tube further includes a first bore configured to accommodate a light source in electronic communication with the processor. In some such embodiments, the light source is a light emitting diode.

In some embodiments, a first end portion of the first bore includes an aperture configured to accommodate the light source, which exposes an interior of the first bore.

In some embodiments, the mounting section includes a portion of the outer surface of the center shaft that is flat and has spatial dimensions configured to accommodate the sensor.

In some embodiments, the portion of the mounting section is recessed into the center shaft by a first depth.

In some embodiments, the processor is an integrated circuit. In some such embodiments, this integrated circuit includes a transceiver.

In some embodiments, the integrated circuit is an application specific integrated circuit configured, at least in part, to control the light source.

In some embodiments, the handle tube is between about 40 centimeters and about 80 centimeters in length. Moreover, the handle tube has a diameter of between about 3 centimeters and about 5 centimeters.

In some embodiments, the exercise bar further includes a first band arm fitted onto the first end of the center shaft. Additionally, in such embodiments, the exercise bar includes a second band arm fitted onto the second end of the center shaft.

Another aspect of the present disclosure is directed to providing an exercise kit. The exercise kit includes an exercise bar of the present disclosure. Moreover, the exercise kit includes a base having a bottom face. The bottom face includes a groove. Additionally, in some embodiments, the exercise kit includes one or more elastic bands. Each respective elastic band in the one or more elastic bands is configured to removably couple the base to the exercise bar by fitting the respective elastic band into the groove of the base and through the first and second band arm.

Yet another aspect of the present disclosure is a method for providing sensory feedback at an exercise bar. The method includes offsetting a longitudinal axis of a center shaft of the exercise bar. Moreover, the method includes determining an amount of a strain on the exercise bar when offsetting of the longitudinal axis of the center shaft. This determining the amount of the strain is by a processor in electronic communication with a sensor coupled to the center shaft. Furthermore, the method includes communicating, by the processor, one or more instructions causing a controller to change a respective state of a sensory output mechanism of the exercise bar based on the determined amount of the strain. The one or more instructions is configured to cause a user operating the exercise bar to sense the change in the respective state of the sensory output mechanism.

In some embodiments, the communicating further includes communicating, by a communications network, to a remote device a plurality of data elements obtained or derived from the sensor during the offsetting of the longitudinal axis. In some such embodiments, the plurality of data elements includes a maximum data element in the plurality of data elements. In some such embodiments, the plurality of data elements includes a period of time associated with the plurality of data elements. In some embodiments, this period of time associated with the plurality of data elements includes a first period of time of the offsetting the longitudinal axis of the center shaft with a phase of the offsetting the longitudinal axis of the center shaft or an average period of time associated with the phase of the offsetting the longitudinal axis of the center shaft. In some such embodiments, the phase of the offsetting the longitudinal axis of the center shaft is an eccentric phase, a concentric phase, an isometric phase, or a combination thereof.

In some embodiments, the communicating the one or more instructions further includes displaying, at the remote device, a digital representation of the plurality of data elements. In some such embodiments, the digital representation includes a table, a chart, a graph, or a combination thereof.

In some embodiments, the method further includes repeating the offsetting the longitudinal axis of the center shaft, the determining the amount of the strain, and the communicating the one or more instructions, and dynamically updating the digital representation responsive to the repeating.

In some embodiments, the remote device is a smartphone device.

In some embodiments, the change in the respective state of the sensory output mechanism includes firing the sensory output mechanism.

In some embodiments, the firing the sensory output mechanism includes, in accordance with a determination that each threshold condition in a first set of threshold conditions, in a plurality of threshold conditions, is satisfied, firing a first configuration of the sensory output mechanism. Furthermore, the one or more instructions for controlling the sensory output mechanism includes, in accordance with a determination that each threshold condition in a second set of threshold condition, in the plurality of threshold conditions, is satisfied, firing a second configuration of the sensory output mechanism.

In some embodiments, a first threshold condition in the plurality of threshold conditions is associated with a threshold strain.

In some embodiments, the first configuration of the sensory output mechanism is an unpowered state.

In some embodiments, the first configuration is associated with a first frequency of firing the sensory output mechanism and the second configuration is associated with a second frequency of firing the sensory output mechanism less than the first frequency.

In some embodiments, the first frequency is in a range of from about 10 Hertz (Hz) to about 60 Hz.

In some embodiments, the first configuration is associated with a first amplitude of firing the sensory output mechanism and the second configuration is associated with a second amplitude of firing the sensory output mechanism less than the first amplitude.

In some embodiments, the first amplitude is in a range of from about 0.5 millimeter (mm) to about 2.5 mm.

In some embodiments, the first configuration is associated with a first sequence of firing the sensory output mechanism and the second configuration is associated with a second sequence of firing the sensory output mechanism different from the first sequence.

In some embodiments, the first sequence is a periodic sequence of firing the sensory output mechanism and the second sequence is a non-periodic sequence of firing the sensory output mechanism.

In some embodiments, the first configuration is associated with a first audio waveform provided when firing the sensory output mechanism and the second configuration is associated with a second audio waveform when firing the sensory output mechanism different from the first audio waveform.

In some embodiments, the sensory output mechanism includes an audio sensory output mechanism, a light source sensory output mechanism, or a vibration sensory output mechanism.

In some embodiments, the strain is tensile.

In some embodiments, the offsetting includes a vertical displacement of the longitudinal axis.

In some embodiments, the sensory output mechanism includes one or more light output mechanisms, one or more vibration output mechanisms, one or more audio output mechanisms, or a combination thereof.

Yet another aspect of the present disclosure is directed to providing an exercise computer system. The exercise computer system includes one or more processors and a memory storing at least one program for execution by the one or more processors. The at least one program includes instructions for determining, responsive to an offsetting of a longitudinal axis of a center shaft of an exercise bar, by the one or more processors in electronic communication with a sensor coupled to the center shaft, an amount of a strain on the exercise bar. Moreover, the at least one program includes instructions for communicating, by the processor, one or more instructions causing a controller to change a respective state of a sensory output mechanism of the exercise bar based on the determined amount of the strain. The one or more instructions is configured to cause a user operating the exercise bar to sense the change in the respective state of the sensory output mechanism.

Yet another aspect of the present disclosure is directed to providing a non-transitory computer readable storage medium stored on an exercise computer system. The exercise computer system includes one or more processors and a memory storing at least one program for execution by the one or more processors. The at least one program includes instructions for determining, responsive to an offsetting of a longitudinal axis of a center shaft of an exercise bar, by the one or more processors in electronic communication with a sensor coupled to the center shaft, an amount of a strain on the exercise bar. Moreover, the at least one program includes instructions for communicating, by the processor, one or more instructions causing a controller to change a respective state of a sensory output mechanism of the exercise bar based on the determined amount of the strain. The one or more instructions is configured to cause a user operating the exercise bar to sense the change in the respective state of the sensory output mechanism.

Yet another aspect of the present disclosure is directed to providing a method for displaying exercise information at a computer system. The computer system includes a display, one or more processors, and a memory storing at least one program for execution by the one or more processors. The at least one program includes instructions for receiving, in electronic format, from an exercise bar, a plurality of data elements captured, at least in part, when offsetting a longitudinal axis of the exercise bar. The at least one program further includes instructions for generating, by one or more models, from a set of data elements in the plurality of data elements, a digital representation of the set of data elements. Additionally, the at least one program includes instructions displaying, on the display, the digital representation of the set of data elements. The display of the digital representation includes a chart. The chart includes a plurality of nodes at least one edge connecting a respective node in the plurality of nodes to at least one other node. Each respective node in the plurality of nodes represents a corresponding data element in the set of data elements.

In some embodiments, the plurality of data elements includes a first set of data elements associated with a strain of the exercise bar when offsetting of the longitudinal axis of the exercise bar.

In some embodiments, the strain in tensile.

In some embodiments, the offsetting includes a vertical displacement of the longitudinal axis of the exercise bar.

In some embodiments, the corresponding data element represented by the respective node is associated with a vertical displacement of the longitudinal axis of the exercise bar.

In some embodiments, the corresponding data element represented by the respective node is associated with a vertical displacement of the longitudinal axis in substantially real-time.

In some embodiments, the corresponding data element represented by the respective node is associated with a maximum strain when offsetting of the longitudinal axis of the exercise bar.

In some embodiments, the corresponding data element represented by the respective node is associated with a period of time associated with the offsetting of the longitudinal axis of the exercise bar.

In some embodiments, the period of time includes a first period of time of the offsetting of the longitudinal axis during the receiving the plurality of data elements with a phase of the offsetting of the longitudinal axis during the receiving the plurality of data elements or an average period of time associated with the phase of the offsetting of the longitudinal axis during the receiving the plurality of data elements.

In some embodiments, the phase of the offsetting of the offsetting of the longitudinal axis during the receiving the plurality of data elements is an eccentric phase, a concentric phase, an isometric phase, or a combination thereof.

In some embodiments, the method further includes repeating the receiving of the plurality of data elements, the generating the digital representation, and the displaying the digital representation, and dynamically updating the digital representation responsive to the repeating.

In some embodiments, the generating the digital representation further includes generating, by the one or more models, the digital representation from: the set of data elements; a historical set of data elements from a previous instance of the receiving of the plurality of data elements, the generating the digital representation, and the displaying the digital representation; a resistance applied to the exercise bar; and a type of exercise performed by a user of the exercise bar when performing the method.

In some embodiments, the generating the digital representation further includes evaluating, by the one or more models, the set of data elements, and, in accordance with a determination that each threshold condition in a first set of threshold conditions, in a plurality of threshold conditions, is satisfied, generating one or more instructions for firing a first configuration of a sensory output mechanism of the exercise bar.

In some embodiments, the method further includes communicating, in electronic format, the one or more instructions for firing the first configuration to the exercise bar.

In some embodiments, the sensory output mechanism of the exercise bar includes one or more light sensory output mechanisms, one or more vibration sensory output mechanisms, one or more audio sensory output mechanisms, or a combination thereof.

In some embodiments, the computer system includes a smartphone device.

In some embodiments, the set of data elements is selected from the plurality of data elements by the one or more models based on a selection by the user for the digital representation.

Yet another aspect of the present disclosure is directed to providing a computer system that includes a display, one or more processors, and a memory storing at least one program for execution by the one or more processors. The at least one program includes instructions for receiving, in electronic format, from an exercise bar, a plurality of data elements captured, at least in part, when offsetting a longitudinal axis of the exercise bar. The at least one program further includes instructions for generating, by one or more models, from a set of data elements in the plurality of data elements, a digital representation of the set of data elements. Additionally, the at least one program includes instructions for displaying, on the display, the digital representation of the set of data elements. The display of the digital representation includes a chart. The chart includes a plurality of nodes at least one edge connecting a respective node in the plurality of nodes to at least one other node. Each respective node in the plurality of nodes represents a corresponding data element in the set of data elements.

Still another aspect of the present disclosure provides a non-transitory computer readable storage medium stored on a computer system. The computer system includes a display, one or more processors, and a memory storing at least one program for execution by one or more processors. The at least one program includes instructions for receiving, in electronic format, from an exercise bar, a plurality of data elements captured, at least in part, when offsetting a longitudinal axis of the exercise bar. The at least one program further includes instructions for generating, by one or more models, from a set of data elements in the plurality of data elements, a digital representation of the set of data elements. Additionally, the at least one program includes instructions for displaying, on the display, the digital representation of the set of data elements. The display of the digital representation includes a chart. The chart includes a plurality of nodes at least one edge connecting a respective node in the plurality of nodes to at least one other node. Each respective node in the plurality of nodes represents a corresponding data element in the set of data elements.

BRIEF DESCRIPTION OF THE DRAWINGS

FIG. 8A illustrates an exploded view of an exemplary exercise bar, in accordance with an embodiment of the present disclosure;

FIG. 11 illustrates a first flow chart of methods for providing sensory feedback at an exercise bar, in accordance with an embodiment of the present disclosure, in which optional steps or embodiments are indicated by dashed boxes;

FIG. 12 illustrates a first flow chart of methods for displaying exercise information at a computer system, in accordance with an embodiment of the present disclosure, in which optional steps or embodiments are indicated by dashed boxes;

Figure 1:
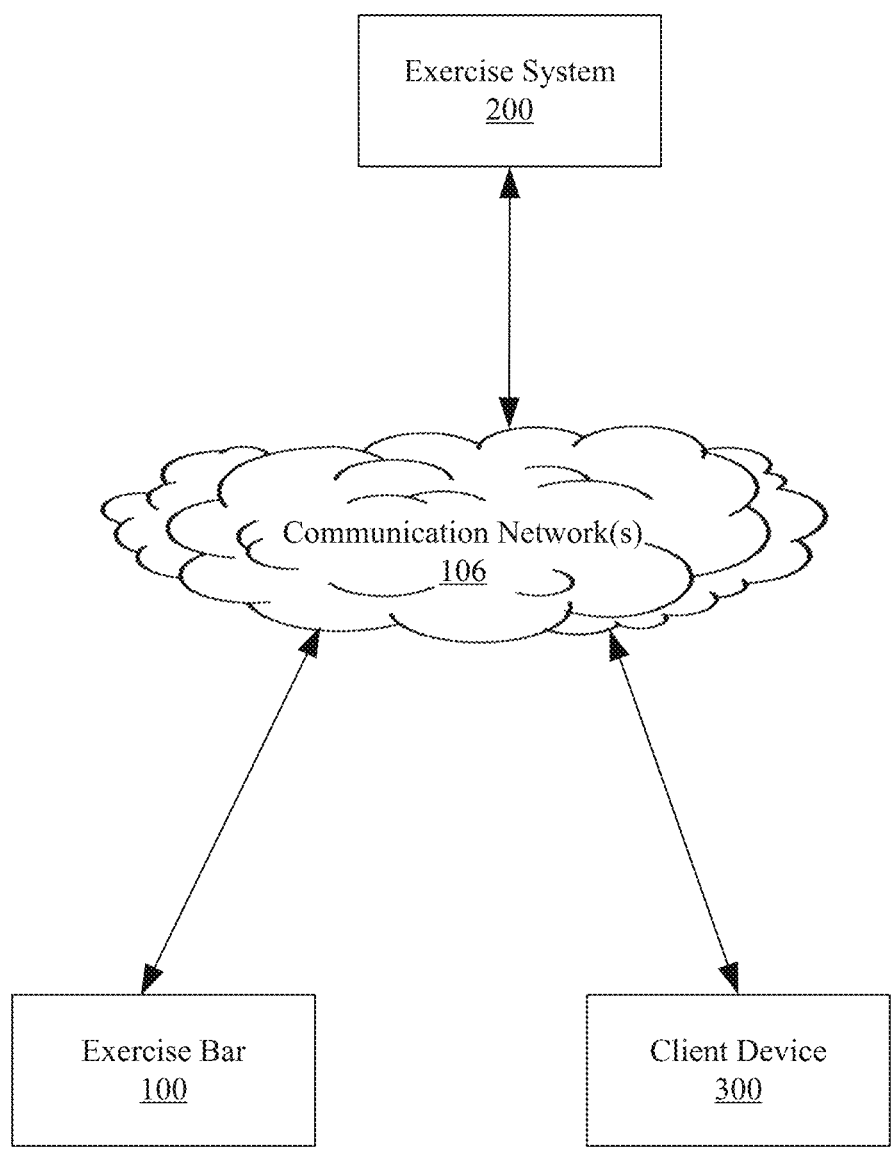
FIG. 1 illustrates a block diagram illustrating an embodiment of a system for displaying exercise information, in accordance with an embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DESCRIPTION OF EMBODIMENTS

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Plural instances may be provided for components, operations or structures described herein as a single instance. Finally, boundaries between various components, operations, and data stores are somewhat arbitrary, and particular operations are illustrated in the context of specific illustrative configurations. Other forms of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first handle could be termed a second handle, and, similarly, a second handle could be termed a first handle, without departing from the scope of the present disclosure. The first handle and the second handle are both handles, but they are not the same handle.

Furthermore, the terms "client," "exerciser," "end user," and "user" as used herein are interchangeable.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

For purposes of explanation, numerous specific details are set forth in order to provide an understanding of various implementations of the inventive subject matter. It will be evident, however, to those skilled in the art that implementations of the inventive subject matter may be practiced without these specific details. In general, well-known structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. Where particular values are described in the application and claims, unless otherwise stated, the term "about" means within an acceptable error range for the particular value. The term "about" can have the meaning as commonly understood by one of ordinary skill in the art. The term "about" can refer to ±10%. The term "about" can refer to ±5%.

As used herein, the term "dynamically" means an ability to update a program while the program is currently running.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$; $n \geq 1 \times 10^6$; $n \geq 5 \times 10^6$; or $n \geq 1 \times 10^7$. In some embodiments n is between 10,000 and $1 \times 10^7$, between 100,000 and $5 \times 10^6$, or between 500,000 and $1 \times 10^6$.

Furthermore, when a reference number is given an "$i^{th}$" denotation, the reference number refers to a generic component, set, or embodiment. For instance, an exercise termed "exercise i" refers to the $i^{th}$ exercise in a plurality of exercises (e.g., an exercise 214-$i$ in a plurality of exercises 214).

For convenience in explanation and accurate definition in the appended claims, the terms "upper," "lower," "up," "down," "upwards," "downwards," "laterally, "longitudinally," "inner," "outer," "inside," "outside," "inwardly," "outwardly," "interior," "exterior," "front," "rear," "back," "forwards," and "backwards" are used to describe features of the exemplary embodiments with reference to the positions of such features as displayed in the figures.

In the present disclosure, unless expressly stated otherwise, descriptions of devices and systems will include implementations of one or more computers. For instance, and for purposes of illustration in FIG. 1, an exercise system 200 is represented as single device that includes all the functionality of the exercise system 200. However, the present disclosure is not limited thereto. For instance, the functionality of the exercise system 200 may be spread across any number of networked computers and/or reside on each of several networked computers and/or by hosted on one or more virtual machines and/or containers at a remote location accessible across a communications network (e.g., communications network 106). One of skill in the art will appreciate that a wide array of different computer topologies is possible for the exercise system 200, and other devices and systems of the preset disclosure, and that all such topologies are within the scope of the present disclosure.

In general, an exercise bar of the present disclosure enables an end-user to perform a variety of exercises at a multitude of resistance ranges.

FIG. 1 depicts a block diagram of a distributed client-server system (e.g., distributed client-server system 10) according to some embodiments of the present disclosure. The system 10 facilitates determining an amount of strain on an exercise bar (e.g., exercise bar 100 of FIG. 1, exercise bar 100 of FIGS. 2A and 2B, exercise bar 100 of FIG. 5, exercise bar 100 of FIG. 10, etc.), controlling a sensory output mechanism based on the determined amount of the strain, receiving a plurality of elements (e.g., associated with the determined amount of the strain), generating a digital representation of a set of data elements from the set of data elements in the plurality of data elements, displaying the digital representation of the set of data elements, or a combination thereof.

Of course, other topologies of the system 10 are possible. For instance, in some embodiments, one or more of the illustrated devices and systems can in fact constitute several computer systems that are linked together in a network or be a virtual machine and/or container in a cloud-computing environment. Moreover, rather than relying on a physical communications network 106, the illustrated devices and systems may wirelessly transmit information between each other. As such, the exemplary topology shown in FIG. 1 merely serves to describe the features of an embodiment of the present disclosure in a manner that will be readily understood to one of skill in the art.

In some embodiments, the communication network 106 optionally includes the Internet, one or more local area networks (LANs), one or more wide area networks (WANs), other types of networks, or a combination of such networks.

Examples of communication networks 106 include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Now that a distributed client-server system 10 has generally been described, exemplary circuitry of an exercise bar 100 for obtaining a plurality of elements associated with a strain on the exercise bar 100 will be described with reference to FIGS. 2A and 2B.

In various embodiments, the circuitry of the exercise bar 100 includes one or more processing units (CPUs) 272, a network or other communications interface 274, and memory 292.

In some embodiments, the circuitry of the exercise bar 100 includes a power system 240 that optionally includes a power management system, one or more power sources (e.g., battery, alternating current (AC)), a recharging system, a power failure detection circuit, a power converter or inverter, a power status indicator (e.g., light source sensory output mechanism 190) and any other components associated with the generation, management, and distribution of power in the exercise bar 100. In this way, the power system 240 is capable of providing power to the exercise bar 100 through the power system 418, allowing the systems and methods of the present disclosure to perform various tasks (e.g., block 1106 of FIG. 11, block 1108 of FIG. 11, block 1206 of FIG. 12, etc.), such as communicating, by the processor 272, one or more instructions for controlling the sensory output mechanism 190 based on a determined an amount of strain applied to the exercise bar 100 without restriction to a wired power supply, such as an electrical outlet. Moreover, in some embodiments, by allowing the exercise bar 100 to utilize the power system 240, the exercise bar 100 further utilizes one or more sensors (e.g., sensor 180 of FIG. 8B) of the exercise without requiring the one or more sensors ancillary to the exercise bar 100, and power for the one or more sensors 180, of the exercise bar 100 itself.

Memory 292 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 292 may optionally include one or more storage devices remotely located from the CPU(s) 272. Memory 292, or alternatively the non-volatile memory device(s) within memory 292, includes a non-transitory computer readable storage medium. Access to memory 292 by other components of the exercise bar 100, such as the CPU(s) 272, is, optionally, controlled by a controller. In some embodiments, memory 292 can include mass storage that is remotely located with respect to the CPU(s) 272. In other words, some data stored in memory 292 may in fact be hosted on devices that are external to the exercise bar 100, but that can be electronically accessed by the exercise bar 100 over an Internet, intranet, or other form of network 106 or electronic cable using communication interface 284.

In some embodiments, the memory 292 of the exercise bar 100 for performing an exercise 214 stores:
- an optional operating system 203 (e.g., ANDROID, iOS, DARWIN, RTXC, LINUX, UNIX, OS X, WINDOWS, or an embedded operating system such as VxWorks) that includes procedures for handling various basic system services;
- an electronic address 204 associated with exercise bar 100 that identifies exercise bar 100 within the distributed system 10;
- a user profile library 206 that stores a plurality of user profiles 208, each user profile 208 associated a corresponding user of the distributed system 10 and further associated with an exercise historical data set 210 associated with a historical performance by the corresponding user, such as when engaging with the exercise bar 100;
- an exercise library 212 that includes a plurality of exercises 214 that is performed with the exercise bar 100, each exercise 214 of the exercise library 212 includes information associated with performance of a respective exercise 214;
- a threshold condition library 216 that stores a plurality of threshold conditions 218, each threshold condition 218 configured to define a criterion for controlling a state of the exercise bar 100;
- a sensory control module 220 configured to control a state of one or more sensory output mechanisms (e.g., sensory output mechanism 190 of FIG. 7, sensory output mechanism 190 of FIG. 8A, sensory output mechanism 190 of FIG. 10, etc.) of the exercise bar 100; and
- a model library 220 that stores a plurality of models 222 for processing information and producing a data set as a result of this processing.

Figure 2A:
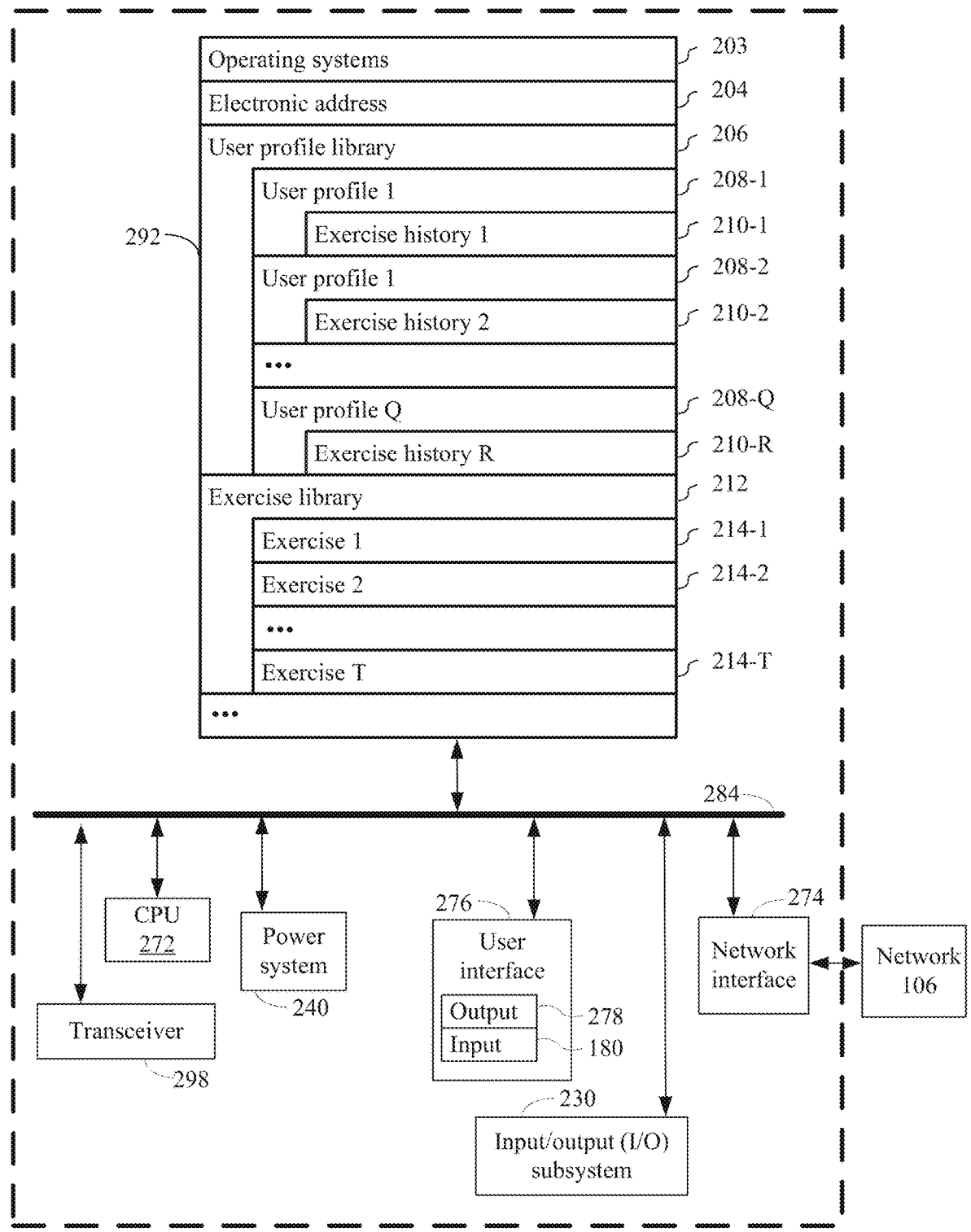
FIGS. 2A and 2B collectively illustrate electronic components of an exercise bar for generating exercise information, in accordance with an embodiment of the present disclosure.

As illustrated in FIG. 2A, the circuitry for the exercise bar 100 optionally includes an operating system 203 that includes procedures for handling various basic system services. The operating system 203 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components of the exercise bar 100. In some embodiments the circuitry for the exercise bar does not include an operating system 203.

In some embodiments, an electronic address 204 is associated with the exercise bar 100. The electronic address 104 is utilized to at least uniquely identify the exercise bar 100 from other devices and components of the distributed system 10 (e.g., uniquely identify first exercise bar 100-1 from second exercise bar 100-2 and third exercise bar 100-3). For instance, in some embodiments, the electronic address 104 is utilized to receive a request from a client device 300 to display a digital representation based on a set of data elements captured at the exercise bar 100. In some embodiments, the exercise bar 100 does not have an electronic address 204.

Figure 13:
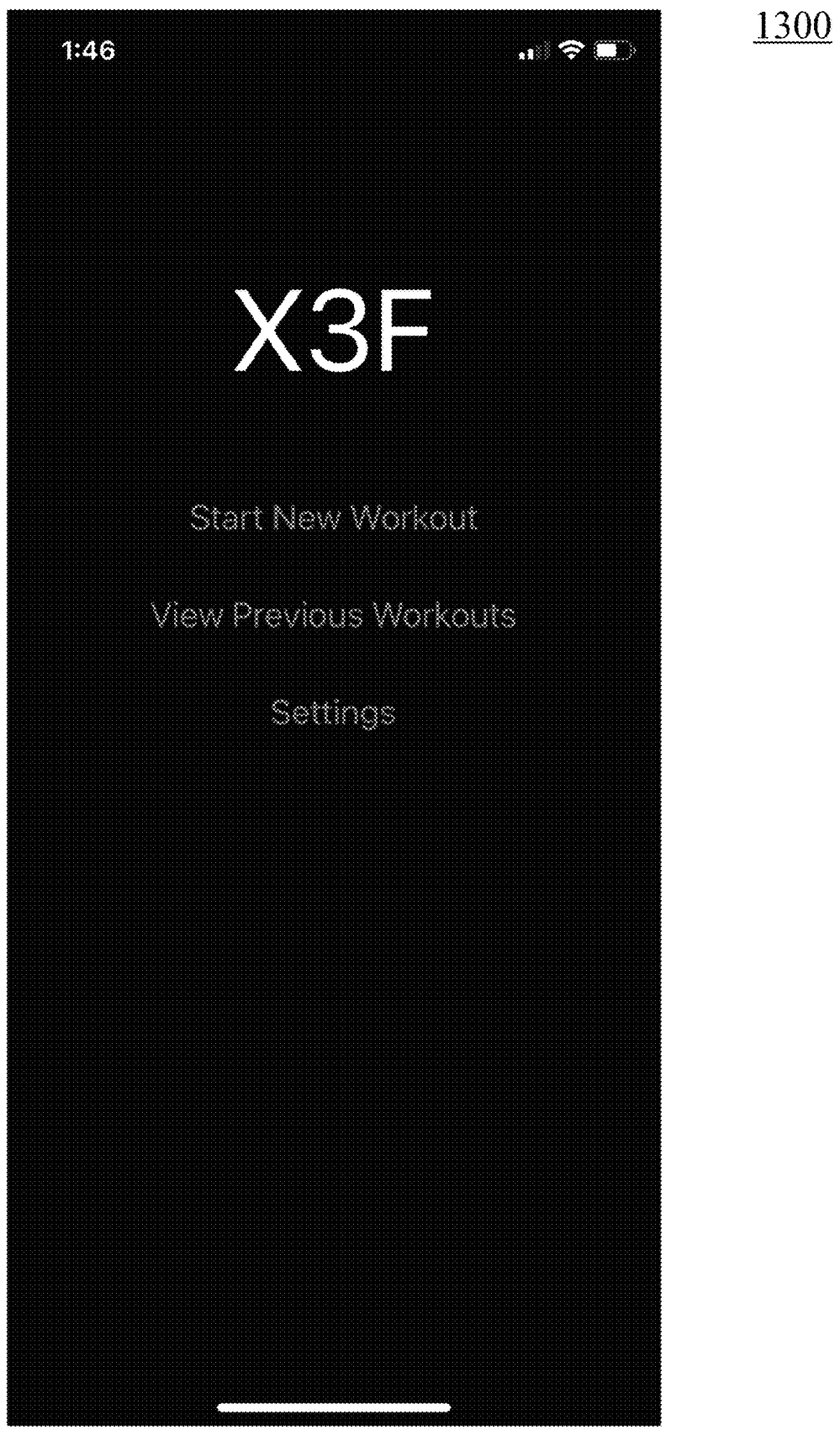
FIG. 13 illustrates a user interface for displaying a first portion of a client application, in accordance with an embodiment of the present disclosure.
Figure 14:
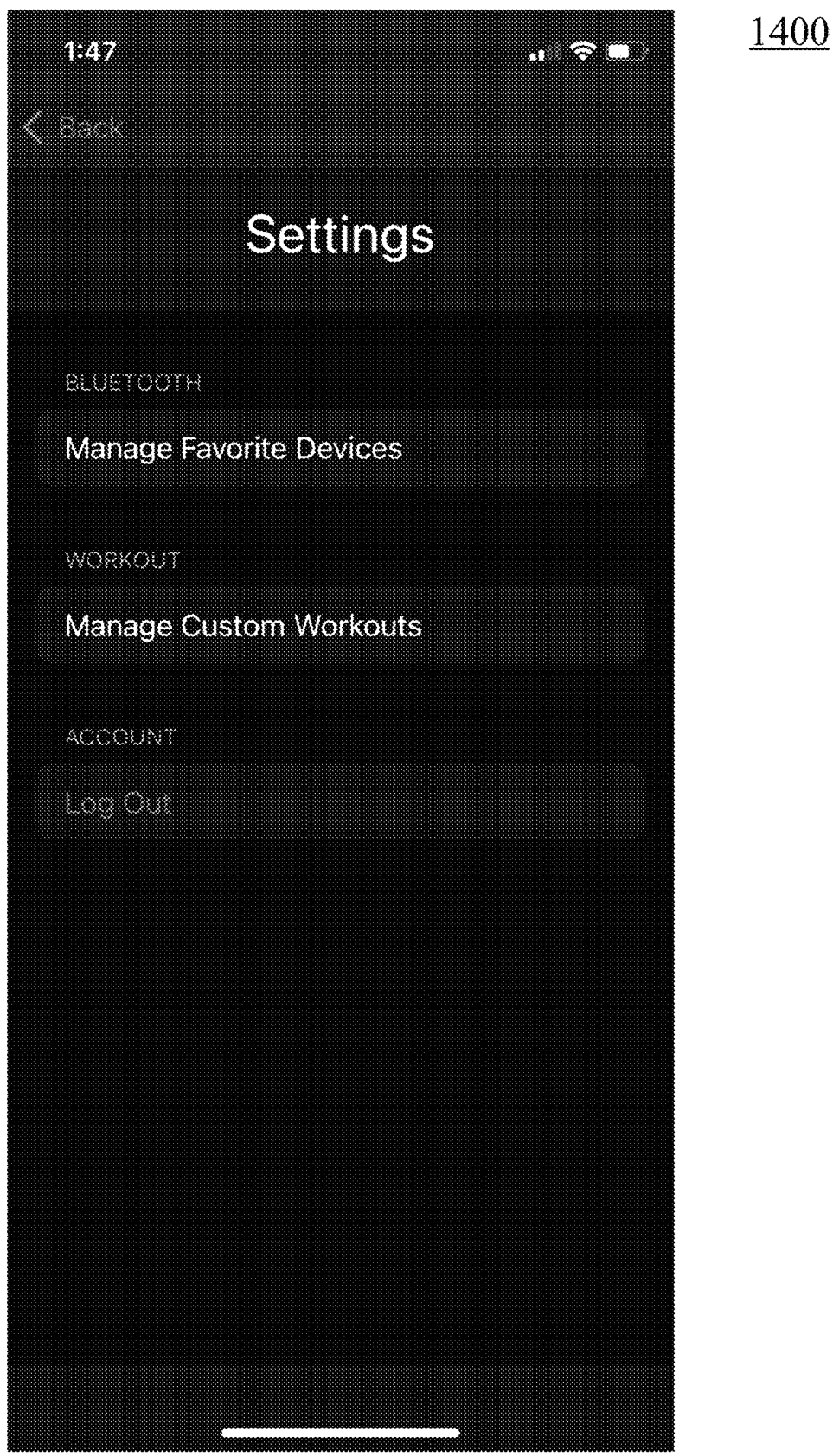
FIG. 14 illustrates a user interface for configuring a client device, in accordance with an embodiment of the present disclosure.

In some embodiments, the user profile library 206 includes a plurality of user profiles 208 (e.g., 2, 3, 4, 5, 6, 7, 8, 9, 10, or more user profiles). Each user profile 208 is associated with a corresponding user of the exercise bar 100, such as a first user that is currently using the exercise bar 100 is associated with a first user profile 208-1 and a second user that previously used the exercise bar 100 is associated with a second user profile 208-2. By retaining the plurality of user profiles 208 at the exercise bar 100, an end-user is allowed to retain information pertaining to the corresponding exercise history 210 performance of the end user with a first exercise bar 100-1 and further utilize the retained information at a remote device on a later date, such as a second exercise bar 100-2, the exercise system 200, or a client device 300. In some embodiments, each user profile 208 is associated with a corresponding exercise historical data set 213 (e.g., first user profile 208-1 is associated with corresponding first exercise history 210-1, second user profile 208-2 is associated with corresponding second exercise history 210-2, . . . , user profile Q 208-Q is associated with corresponding exercise history R 210-R of FIG. 2A). For instance, referring briefly to FIG. 13, a user interface 1300 is displayed (e.g., by display 478 of the client device 300) that allows the user to start a new exercise session with the exercise bar 100 through a client application 420 (e.g., obtain and store new data from the sensor 180 of the exercise bar 100) or view previous exercise sessions (e.g., prior data from the sensor 180 of the exercise bar 100). In some embodiments, the corresponding exercise history 210 includes an extremum of a quantity associated with performing a respective exercise 214, such as an absolute power in Watts (W) generated during an exercise by the end-user associated with the user profile 208. Furthermore, in some embodiments, the user profile 208 includes a plurality of characteristics associated with the corresponding user, such as an age of the corresponding user, a weight of the corresponding user, a height of the corresponding user, an activity level of the corresponding user, a nutritional characteristic of the corresponding user, and the like, such as an amount of time spent exercising aerobically or engaging with the exercise bar on a given basis (e.g., every week). In some embodiments, the user profile 208 stores a user login and password for accessing a client application associated with the exercise bar 100 (e.g., client application 420 of FIG. 4, user interface 1300 of FIG. 13, user interface 1400 of FIG. 14, user interface 1500 of FIG. 15, user interface 1600 of FIG. 16, user interface 1700 of FIG. 17, user interface 1800 of FIG. 18, etc.).

Figure 15:
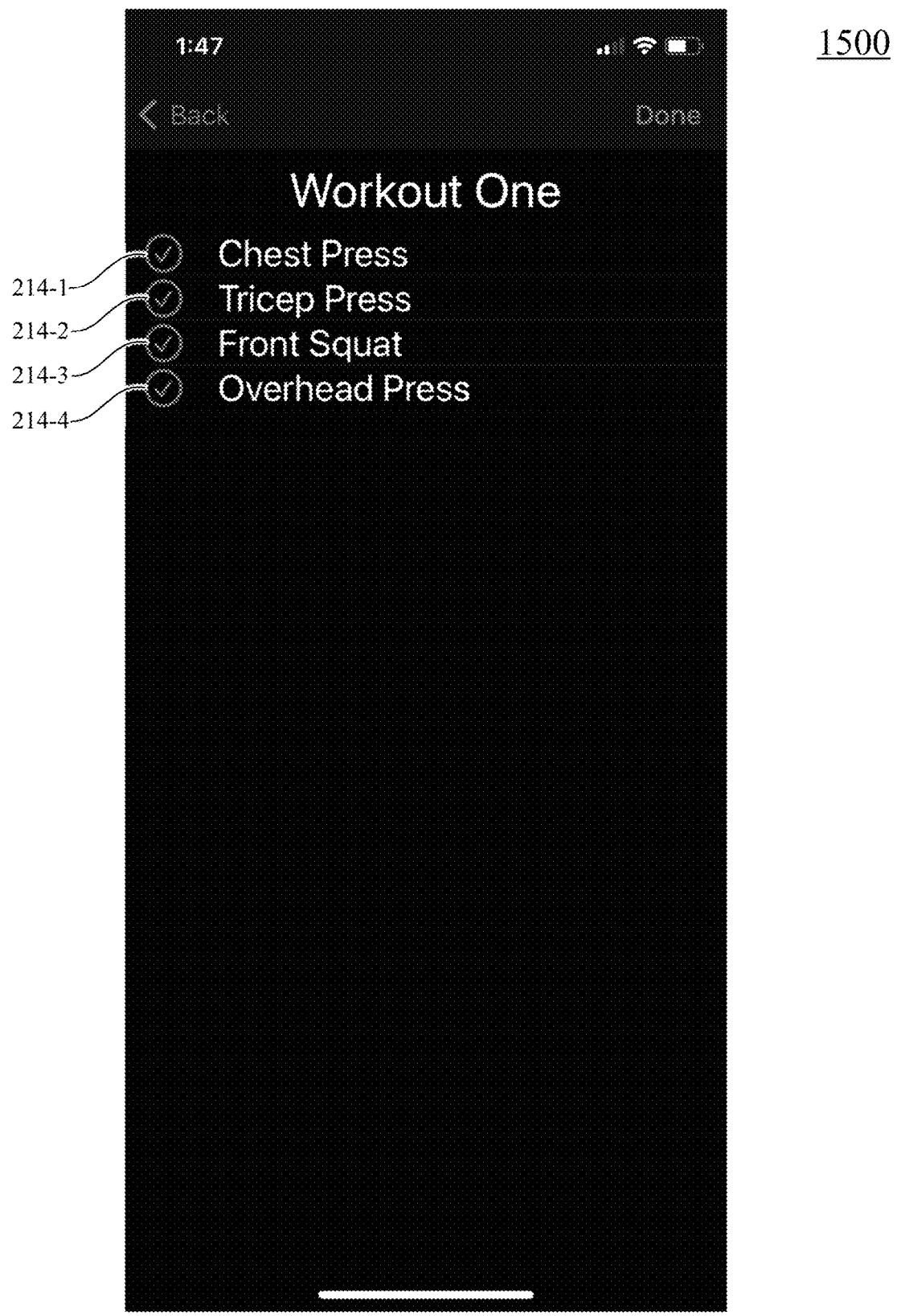
FIG. 15 illustrates a user interface for selecting an exercise to perform when offsetting an exercise bar, in accordance with an embodiment of the present disclosure.

In some embodiments, the circuitry for the exercise bar 100 includes an exercise library 212 that stores information associated with a plurality of exercises 214. Each exercise 214 is configured to be performed with the exercise bar 100. Referring briefly to FIG. 15, a user interface 1500 of a client application 420 is provided that includes a listing of a first exercise 214-1 for chest press for performance with the exercise bar 100, a second exercise 214-2 of tricep press for performance with the exercise bar 100, a third exercise 214-3 of front squat for performance with the exercise bar 100, and a fourth exercise 214-4 of overhead press for performance with the exercise bar 100. Non-limiting examples of some such exercises 214 include performing, with the exercise bar 100 or an exercise kit 600 of the present disclosure, a standing chest press, upright row, split squat (e.g., left legged split squat exercise 214-5 of FIG. 17), triceps pushdown, deadlift (e.g., deadlift exercise 214-6 of FIG. 18), bent over row, biceps curl, calf raise, standing shoulder press, and the like. In some such embodiments, such exercises 214 are performed beginning with a full range of motion, and as fatigue sets in, with diminishing ranges of motion, such as under constant but variable resistance. However, the present disclosure is not limited thereto. In this way, the information associated with each exercise 214 is retained by the circuitry for the exercise bar 100 and further utilized to enhance evaluations of data elements obtained when performing a respective exercise 214. For instance, in some embodiments, each respective exercise 214 includes an exercise name, a range of motion of the respective exercise 214 (e.g., a minimum distance of offsetting a longitudinal axis of the exercise bar 100, a maximum distance of offsetting a longitudinal axis of the exercise bar 100, etc.), a training intensity, a listing of one or more biometric measurements associated with the respective exercise 214, a training regimen of the respective exercise 214 (e.g., a first regimen for developing strength by performing five sets of five repetitions of the respective exercise with 3 minutes recovery between each set and a second regimen for hypertrophy by performing 3 sets of 10 repetitions of the respective exercise 214 with 1 minute recovery between each set, etc.). Additional details and information regarding exercise information stored for a respective exercise 214 can be found at Marston et al., 2017, "A Comparison of Traditional and Novel Metrics to Quantify Resistance Training," Scientific Reports, 7(1), pg. 1, which is hereby incorporated by reference in its entirety.

Figure 2B:
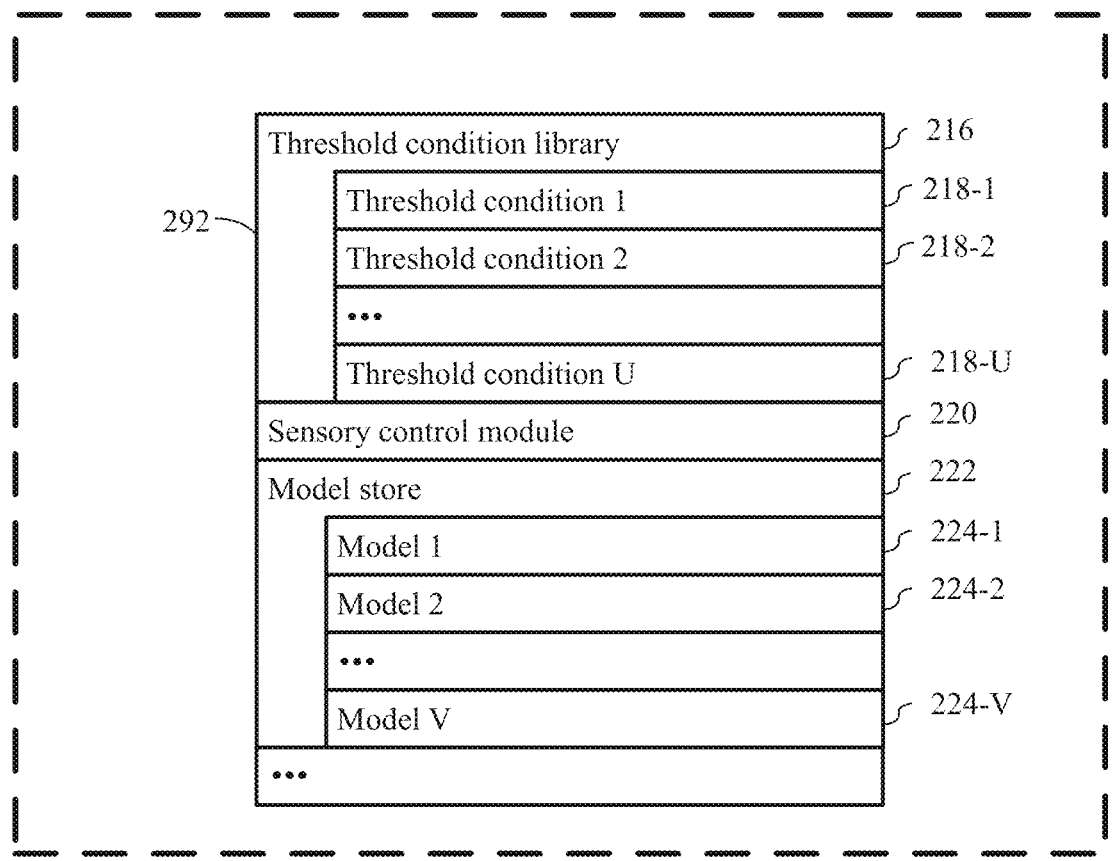

In some embodiments, the circuitry for the exercise bar 100 includes a threshold condition library 216 that is configured to store a plurality of threshold conditions 218 (e.g., first threshold condition 218-1, second threshold condition 218-2 . . . , threshold condition U 218-U of FIG. 2B). Each threshold condition 218 defines a criterion that must be achieved in order for the threshold condition 218 to be deemed satisfied. In some embodiments, a respective threshold condition 218 is based on some Boolean logic, such as an IF statement for controlling the sensory output mechanism 190 in accordance with a first strain applied to the center shaft 150 as measured by the sensor 180 of the exercise bar 100. In some embodiments, the respective threshold condition 218 is configured to improve a quality of an exercise 214 when a user performs the exercise 214 in the future, such as a threshold offsetting of the exercise bar 100 to ensure the user is manipulating the exercise bar 100 through a full range of motion of the exercise 214. In some embodiments, the respective threshold condition 218 is defined by a user, such as an exerciser or an administrator of an exercise system 200. In some embodiments, the respective threshold condition 218 is configured for a corresponding exercise bar 100, a corresponding exercise 214, a corresponding user, or a combination thereof.

The exercise bar 100 includes a sensory control module 220 (e.g., controller) that is configured to modify or cause a change in a state of a respective sensory output mechanism 190 of the exercise bar 100. This causing the change of the state of the respective sensory output mechanism 190 is in accordance with a determination that one or more threshold conditions 218 of the threshold condition library 216 is satisfied. Said otherwise, in some such embodiments, the sensory control module 220 facilitates evaluating a set of threshold conditions 218 in order to allow for changing a state of a respective sensory output mechanism 190 of the exercise bar 100. In some embodiments, the sensory control module 220 changes a power state of the respective sensory output mechanism 190, such as modifying the respective sensory output mechanism between an ON state and an OFF state. However, the present disclosure is not limited thereto. For instance, in some embodiments, the sensory control module 220 disconnects a respective sensory output mechanism 190 from a power supply (e.g., power supply 240 of FIG. 2), such that the sensory output mechanism 190 is completely disabled. In some embodiments, the sensory control module 220 disables the sensory output mechanism 190 by placing the sensory output mechanism 190 in a state of diminished usefulness, which allows for some limited use of the sensory output mechanism 190 (e.g., a power output reduction of 75%). In some embodiments, a light source 190 is limited to a lowest brightness setting and/or less than maximum brightness setting. In some embodiments, a vibration sensory output mechanism 190 is limited to a lowest speed setting (e.g., lowest frequency). In some embodiments, an amount of power generated, stored, or made available for use from the power system 240 for the sensory output mechanism 190 is limited (e.g., to 25% of enabled state) when the sensory output mechanism 190 is placed in a disabled state by the sensory control module 220. However, the present disclosure is not limited thereto.

In some embodiments, the circuitry for the exercise bar 100 includes a model store 222 that is configured to store a plurality of models 224 (e.g., first model 224-1, second model 224-2, . . . , model V 224-V of FIG. 2B, where V is any positive integer greater than 1, such as 5, 10, 15, or greater). In some embodiments, the model store 222 includes one or more computational models 224 for determining a qualitative aspect of using the exercise bar. For instance, in some embodiments, the model store 222 includes a first model 224-1 configured to determine a force applied to the exercise bar 100 (e.g., a maximum tensile strain), a second model 224-2 of a function of a number of repetitions used with the exercise bar 100, a third model 224-3 of a phase of an exercise 214 (e.g., determining a period of time the exercise bar is in an eccentric phase of the exercise 214 or the concentric phase of the exercise 214). However, the present disclosure is not limited thereto. For instance, in some embodiments, a model 224 of the model store 222 includes one or more gradient boosting models, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set including a respective exercise history 214) that includes one or more features identified from a data set. By way of example, in some embodiments, the training data set includes data associated with a first user profile 208-1 and data associated with user tendencies when engaging with the exercise bar 100, such as performance of a first exercise 214-1 with the exercise bar 100. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using, for instance, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as minimum cut, harmonic function, manifold regularization, etc.), heuristic approaches, or support vector machines. In some embodiments, the supervision of a respective model 224 is performed by a coach associated with an end-user of the exercise bar 100 that utilizes the systems and methods of the present disclosure, such as an administrator of an exercise system 200.

Each of the above identified modules and applications correspond to a set of executable instructions for performing one or more functions described above and the methods described in the present disclosure (e.g., the computer-implemented methods and other information processing methods described herein; method 1100 of FIG. 11; method 1200 of FIG. 12; etc.). These modules (e.g., sets of instructions) need not be implemented as separate software programs, procedures or modules, and thus various subsets of these modules are, optionally, combined or otherwise re-arranged in various embodiments of the present disclosure. In some embodiments, the memory 292 optionally stores a subset of the modules and data structures identified above. Furthermore, in some embodiments, the memory 292 stores additional modules and data structures not described above.

It should be appreciated that the circuitry of exercise bar 100 of FIGS. 2A and 2B is only one example of circuitry for the exercise bar 100 of the present disclosure, and that the circuitry for the exercise bar 100 optionally has more or fewer electronic components than shown in FIGS. 2A and 2B, optionally combines two or more such electronic components, or optionally has a different configuration or arrangement of the electronic components. The various electronic components shown in FIGS. 2A and 2B are implemented in hardware, software, firmware, or a combination thereof, including one or more signal processing and/or application specific integrated circuits (e.g., exercise bar 100 of FIG. 5, exercise bar 100 of FIG. 6, exercise bar 100 of FIG. 7, exercise bar 100 of FIG. 8A, exercise bar 100 of FIG. 9, exercise bar 100 of FIG. 10, etc.).

Figure 3:
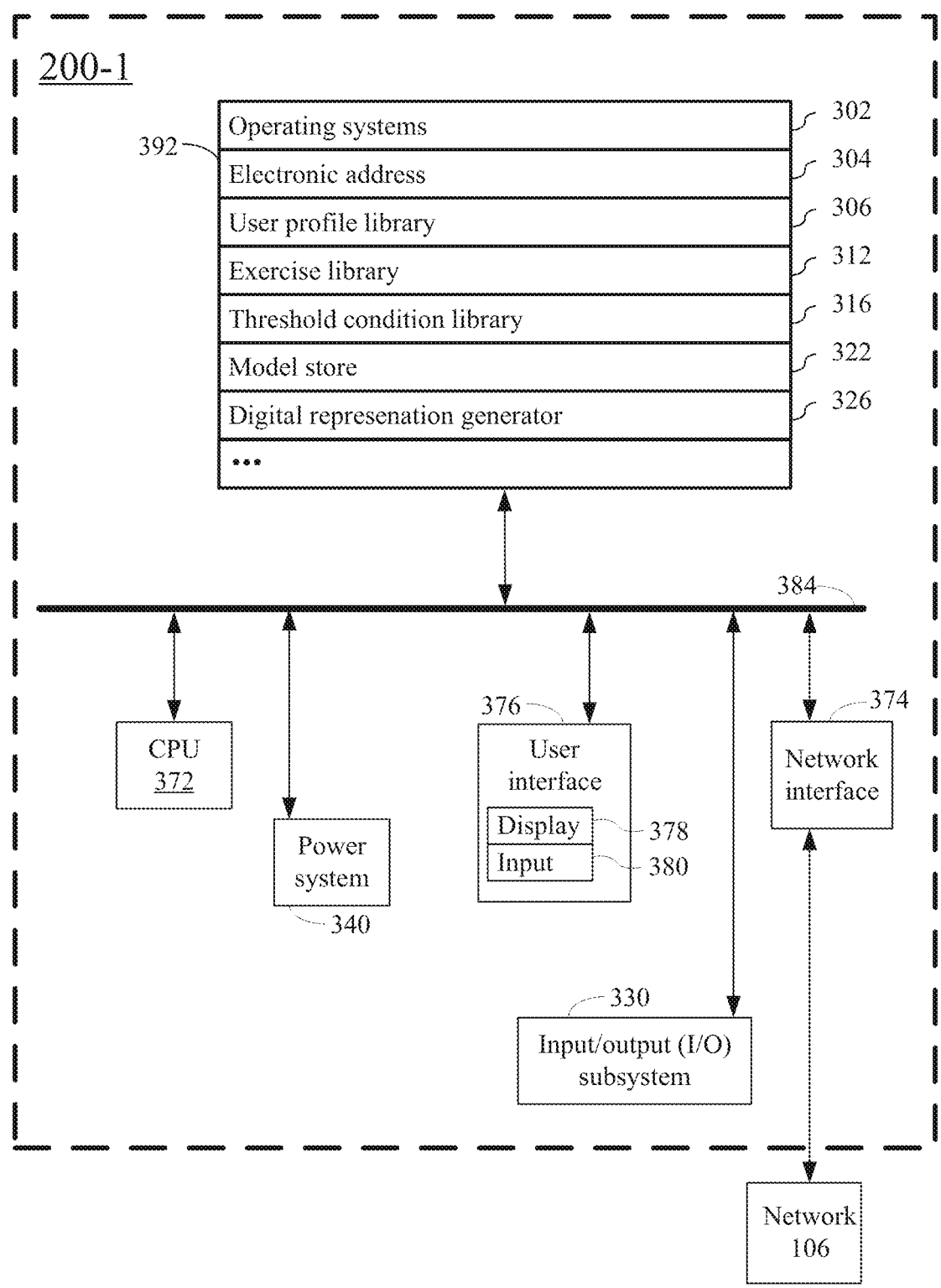
FIG. 3 illustrates an exercise computer system for displaying exercise information, in accordance with an embodiment of the present disclosure.

Now that electronic components of an exercise bar 100 have generally been described, an exemplary exercise system 200 for displaying a digital representation of an amount of strain on the exercise bar 100 and/or communicating one or more instructions for controlling a sensory output mechanism 190 of the exercise bar 100 will be described with reference to FIG. 3.

In various embodiments, the exercise system 200 includes one or more processing units (CPUs) 372, a network or other communications interface 374, and memory 392.

Memory 392 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 392 may optionally include one or more storage devices remotely located from the CPU(s) 372.

Memory 392, or alternatively the non-volatile memory device(s) within memory 392, includes a non-transitory computer readable storage medium. Access to memory 392 by other components of the exercise system 200, such as the CPU(s) 372, is, optionally, controlled by a controller. In some embodiments, memory 392 can include mass storage that is remotely located with respect to the CPU(s) 372. In other words, some data stored in memory 392 may in fact be hosted on devices that are external to the exercise system 200, but that can be electronically accessed by the exercise system 200 over an Internet, intranet, or other form of network 106 or electronic cable using communication interface 374.

In some embodiments, the memory 392 of the exercise system 200 for generating a digital representation of an amount of strain on an exercise bar 100 and/or one or more instructions for controlling a sensory output mechanism 190 of the exercise bar 100 stores:

an operating system 302 (e.g., ANDROID, iOS, DARWIN, RTXC, LINUX, UNIX, OS X, WINDOWS, or an embedded operating system such as VxWorks) that includes procedures for handling various basic system services;

an electronic address 304 associated with the exercise system 200 that identifies the exercise system 200;

a user library 306 that stores a plurality of user profiles 208;

an exercise library 312 that includes a plurality of exercises 214;

a threshold condition library 316 that stores a plurality of threshold conditions 218, each threshold condition configured to define a criterion for controlling a state of the exercise bar 100;

a model store 322 that includes one or more models 224 configured to evaluate a set of data elements to produce a computational result; and a digital representation generator 326 that is configured to produce a digital representation associated with a state of the exercise bar 100, such as a visualization of one or more data elements captured at the exercise bar 100.

In some embodiments, as indicated above, an electronic address 304 is associated with the exercise system 200. The electronic address 304 is utilized to at least uniquely identify the exercise system 200 from other devices and components of the distributed system 10 (e.g., uniquely identify exercise system 200 from client device 300 and exercise bar 100). For instance, in some embodiments, the electronic address 304 is utilized to receive a request from a client device 300 for a digital representation of a set of data elements captured at an exercise bar 100.

In some embodiments, the user library 306 of the exercise system 200 provides similar functionality as the user library 206 of the exercise bar 100.

In some embodiments, the exercise library 312 of the exercise system 200 provides similar functionality as the exercise library 212 of the exercise bar 100.

In some embodiments, the threshold condition library 316 of the exercise system 200 provides similar functionality as the threshold condition library 216 of the exercise bar 100.

In some embodiments, the model store 322 of the exercise system 200 provides similar functionality as the model store 222 of the exercise bar 100.

Figure 16:
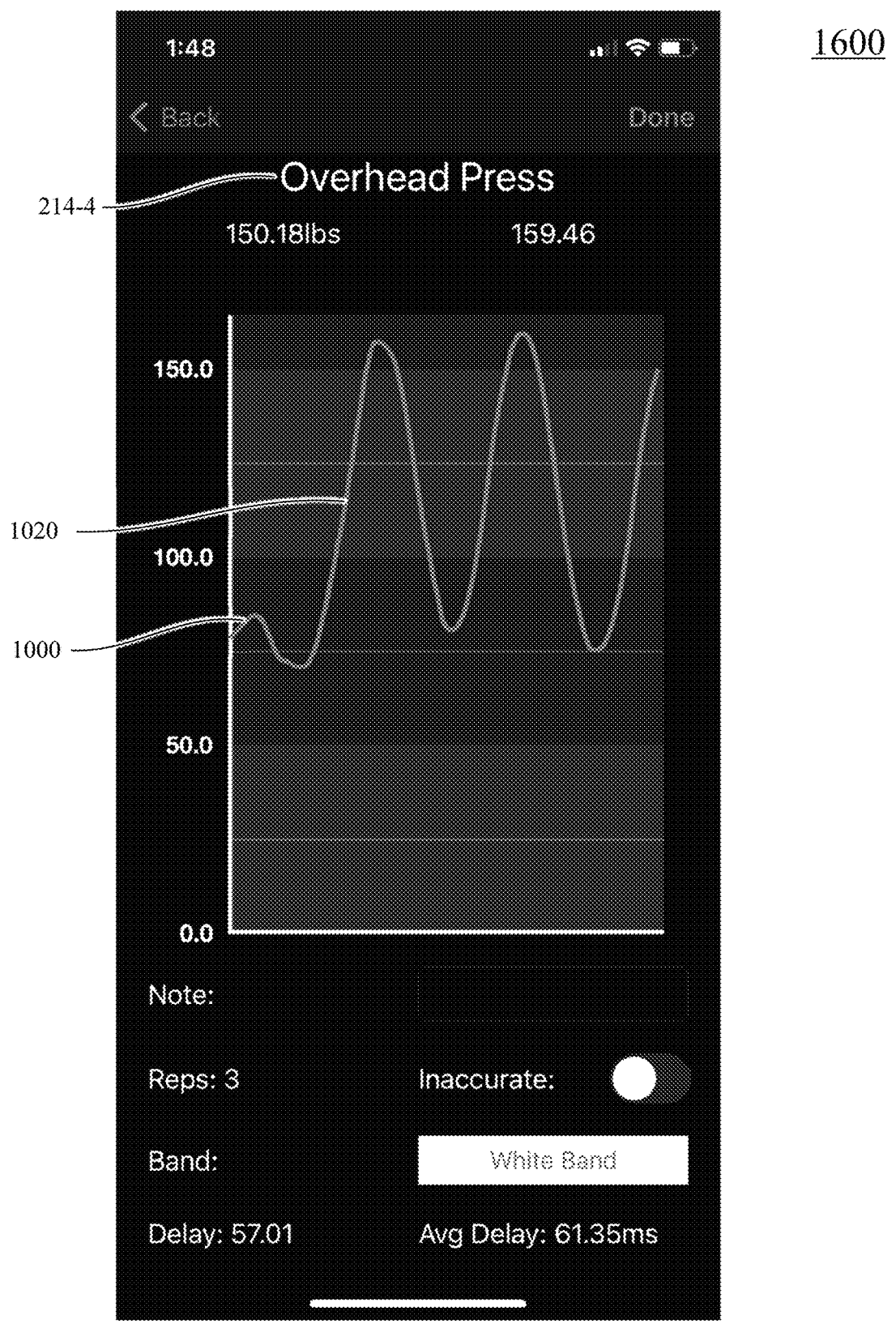
FIG. 16 illustrates a user interface for displaying exercise information when offsetting an exercise bar, in accordance with an embodiment of the present disclosure.
Figure 17:
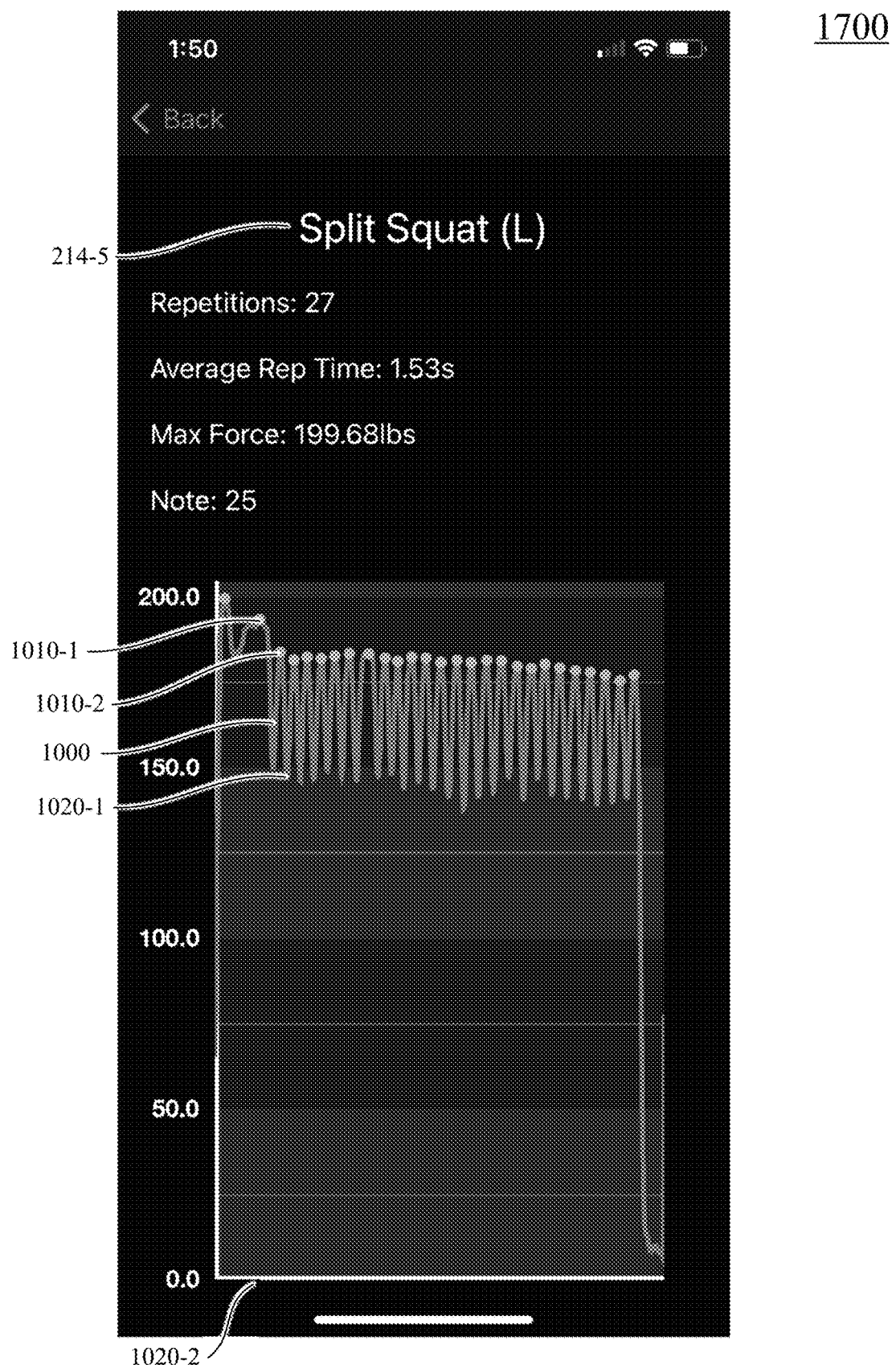
FIG. 17 illustrates another user interface for displaying exercise information when offsetting an exercise bar, in accordance with an embodiment of the present disclosure.
Figure 18:
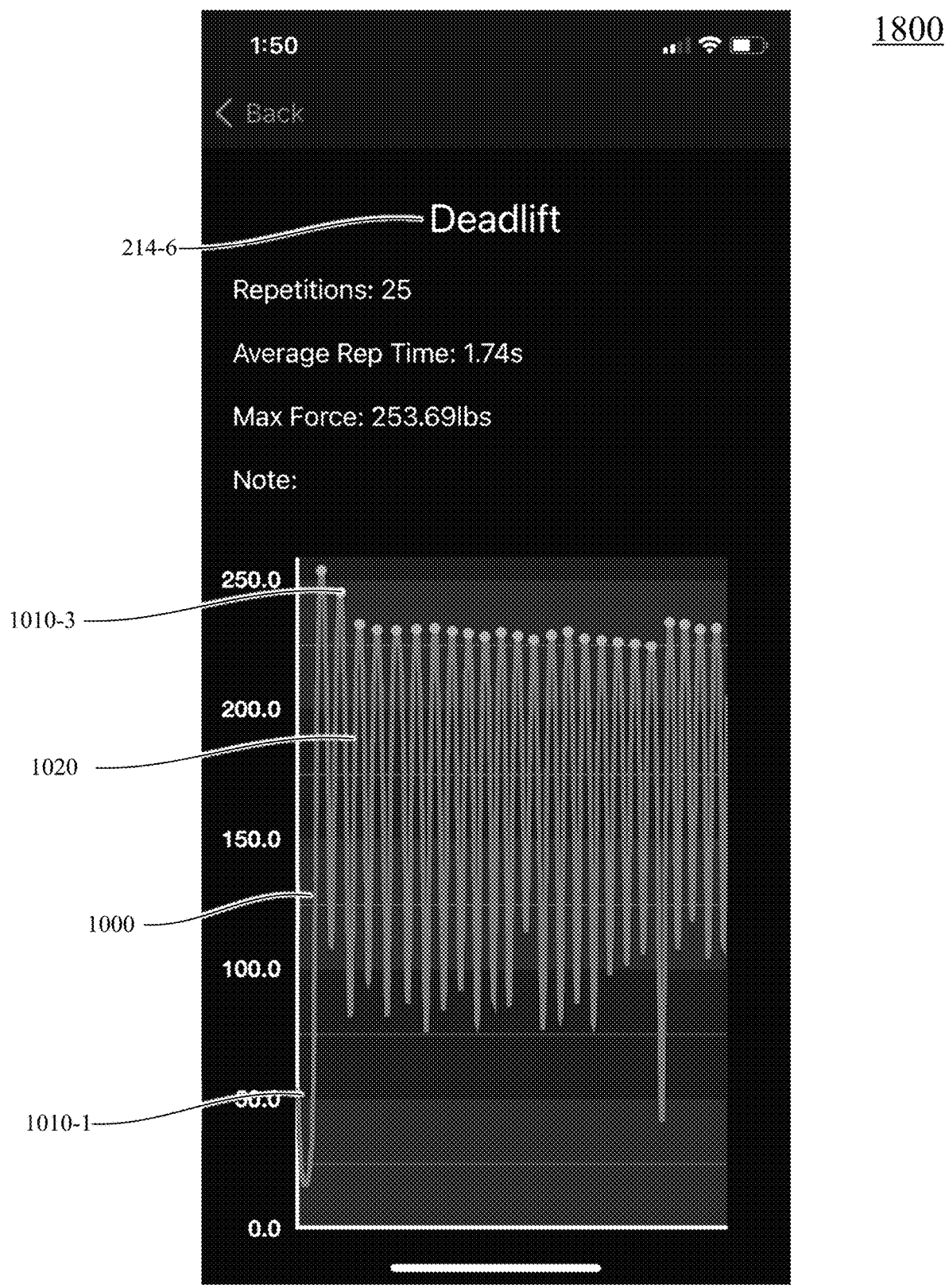
FIG. 18 illustrates a user interface for displaying exercise information when offsetting an exercise bar, in accordance with an embodiment of the present disclosure.

In some embodiments, the exercise system 200 includes a digital representation generator 326 that is configured to produce a digital representation associated with a state of the exercise bar 100 (e.g., digital representation 1000 of FIG. 15, digital representation 1000 of FIG. 16, digital representation 1000 of FIG. 17, digital representation 1000 of FIG. 18, etc.). In some embodiments, each digital representation provides, when displayed through a display, such as display 478 of a client device 300, a visualization of one or more data elements transmitted by the exercise bar 100, such as a first data element captured by the sensor 180 of the exercise bar 100. In some embodiments, each respective digital representation 1000 is characterized by a plurality of nodes (e.g., first node 1010-1 and second node 1010-2 of FIG. 17) that is within a plurality of edges (e.g., first edge 1020-1 and second edge 1020-2 of FIG. 17). In some embodiments, each respective node 1010 is associated with a measurement obtained from the sensor 180 of the exercise bar 100, such as an amount of strain applied to the center shaft 150 of the exercise bar 100. Furthermore, in some embodiments, each respective node 1010 is associated with a unique point in time, which allows for the digital representation to provide a graph of the measurement obtained from the sensor 180 over a period of time that includes each unique point in time associated with a node 1010. In some embodiments, the plurality of nodes 1010 connect to form a continuous line, such as a straight line and/or a curved line.

Figure 4:
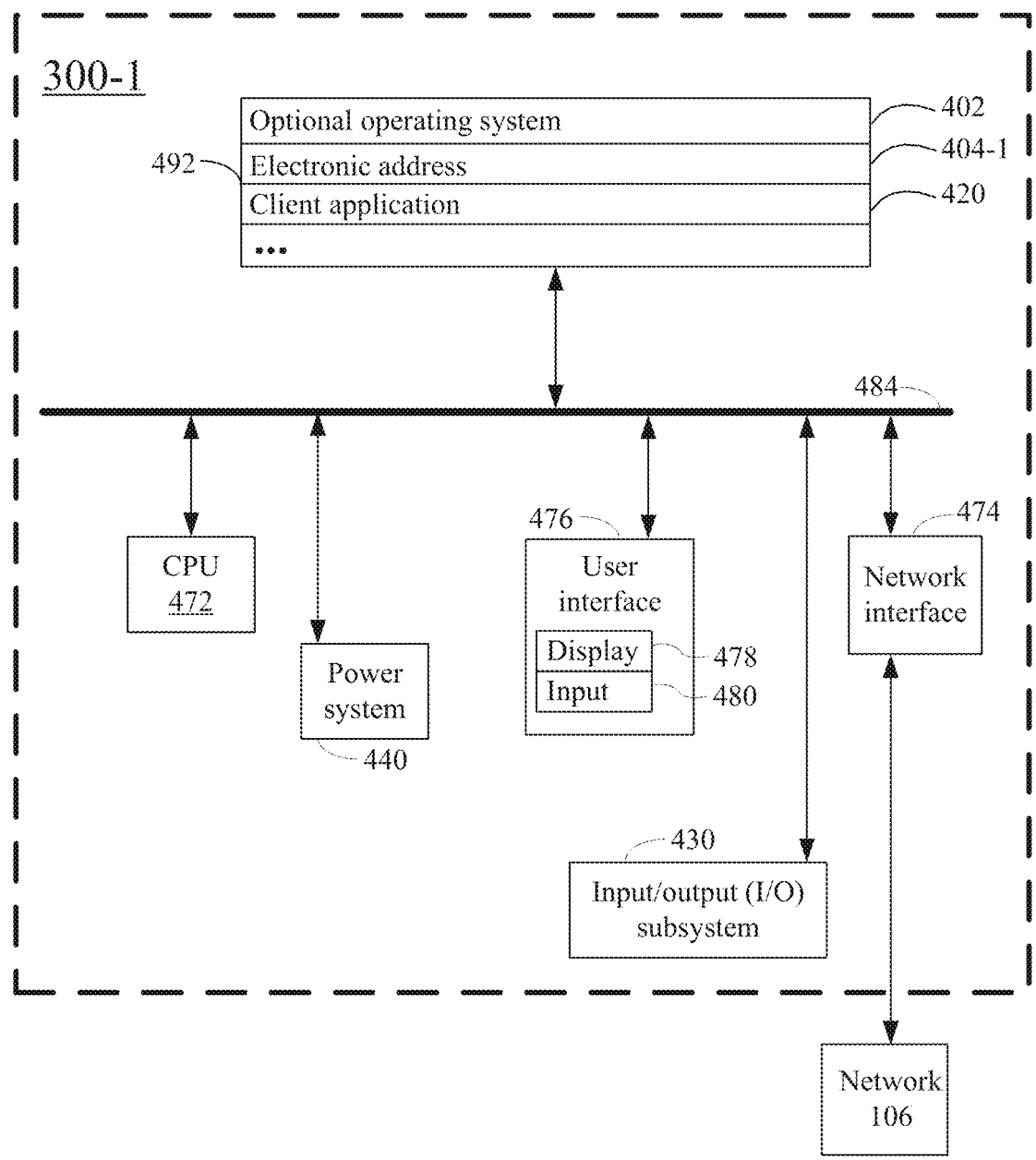
FIG. 4 illustrates a client device for displaying exercise information, in accordance with an embodiment of the present disclosure.

Referring to FIG. 4, an exemplary client device 300 is provided (e.g., first client device 300-1). A client device 300 includes one or more processing units (CPUs) 472, one or more network or other communication interfaces 474, memory 492 (e.g., random access memory and/or non-volatile memory) optionally accessed by one or more controllers, and one or more communication busses 474 interconnecting the aforementioned components.

In some embodiments, a client device 300 includes a mobile device, such as a mobile phone (e.g., smart phone), a tablet, a laptop computer, a wearable device such as a smart watch, and the like. In some embodiments, the client device 300 is a desktop computer or other similar devices. In some embodiments, the client device 300 is a standalone device that is dedicated to performing an exercise 214, such as a squat machine apparatus, of the systems and methods of the present disclosure.

In addition, the client device 300 includes a user interface 476. The user interface 376 typically includes a display device 378 for presenting media, such as the digital representation of the set of data elements obtained from the exercise bar 100. In some embodiments, the display device 478 is optionally integrated within the client device 300 (e.g., housed in the same chassis as the CPU 472 and memory 492), such as a smart (e.g., smart phone) device. In some embodiments, the client device 300 includes one or more input device(s) 480, which allow the subject to interact with the client device 300. In some embodiments, input devices 480 include a keyboard, a mouse, and/or other input mechanisms. Alternatively, or in addition, in some embodiments, the display device 478 includes a touch-sensitive surface, e.g., where display 478 is a touch-sensitive display or client device 300 includes a touch pad.

In some embodiments, the client device 300 includes an input/output (I/O) subsystem 430 for interfacing with one or more peripheral devices with the client device 300. For instance, in some embodiments, audio is presented through an external device (e.g., speakers, headphones, etc.) that receives audio information from the client device 300 and/or a remote device (e.g., exercise bar 100 of FIG. 10, exercise system 200 of FIG. 3), and presents audio data based on this audio information. In some embodiments, the input/output (I/O) subsystem 430 also includes, or interfaces with, an audio output device, such as speakers or an audio output for connecting with speakers, earphones, or headphones. In some embodiments, the input/output (I/O) subsystem 430 also includes voice recognition capabilities (e.g., to supplement or replace an input device 480).

In some embodiments, the client device 300 also includes one or more sensors (e.g., an accelerometer, a magnetometer, a proximity sensor, a gyroscope, etc.), an image capture device (e.g., a camera device or an image capture module and related components), a location module (e.g., a Global Positioning System (GPS) receiver or other navigation or geolocation system module/device and related components), or a combination thereof, and the like.

As described above, the client device 300 includes a user interface 476. The user interface 476 typically includes a display device 378, which is optionally integrated within the client device 300 (e.g., housed in the same chassis as the CPU and memory, such as with a smart phone or an all-in-one desktop computer client device 300). In some embodiments, the client device 300 includes a plurality of input device(s) 480, such as a keyboard, a mouse, and/or other input buttons (e.g., one or more sliders, one or more joysticks, one or more radio buttons, etc.). Alternatively, or in addition, in some embodiments, the display device 478 includes a touch-sensitive surface, e.g., where display 308 is a touch-sensitive display 478 or a respective client device 300 includes a touch pad.

In some embodiments, the client device 300 presents media to a user through the display 478. Examples of media presented by the display 480, such as the digital representation generated at the exercise system 200 based on the set of data elements obtained from the exercise bar 100. As a non-limiting example, in some embodiments, the digital representation include one or more images, a video, audio (e.g., waveforms of an audio sample), or a combination thereof. In typical embodiments, the one or more images, the video, the audio, or the combination thereof is presented by the display 478 through a client application 420. In some embodiments, the audio is presented through an external device (e.g., speakers, headphones, etc.) that receives audio information from the client device 300, the exercise system 200, or both, and presents audio data based on this audio information. In some embodiments, the user interface 476 also includes an audio output device, such as speakers or an audio output for connecting with speakers, earphones, or headphones. In some embodiments, the user interface 476 also includes an audio input device (e.g., a microphone), and optional voice recognition capabilities (e.g., to supplement or replace the keyboard). Optionally, the client device 300 includes an audio input device (e.g., a microphone) to capture audio (e.g., speech from a user). In some embodiments, the audio input device is a single omni-directional microphone.

In some embodiments, the client device 300 also includes one or more of: one or more sensors (e.g., accelerometer, magnetometer, proximity sensor, gyroscope); an image capture device (e.g., a camera device or module and related components); and/or a location module (e.g., a Global Positioning System (GPS) receiver or other navigation or geolocation device and related components). In some embodiments, the sensors include one or more hardware devices that detect spatial and motion information about the client device 300. Spatial and motion information can include information about a position of the client device 300, an orientation of the client device 300, a velocity of the client device 300, a rotation of the client device 300, an acceleration of the client device 300, or a combination thereof.

Memory 492 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 492 may optionally include one or more storage devices remotely located from the CPU(s) 472. Memory 392, or alternatively the non-volatile memory device(s) within memory 492, includes a non-transitory computer readable storage medium. Access to memory 492 by other components of the client device 300, such as the CPU(s) 472 and the I/O subsystem 430, is, optionally, controlled by a controller. In some embodiments, memory 492 can include mass storage that is remotely located with respect to the CPU 472. In other words, some data stored in memory 392 may in fact be hosted on devices that are external to the client device 300, but that can be electronically accessed by the client device 300 over an Internet, intranet, or other form of network 106 or electronic cable using communication interface 484.

In some embodiments, the memory 492 of the client device 300 stores:
an operating system 402 (e.g., ANDROID, iOS, DARWIN, RTXC, LINUX, UNIX, OS X, WINDOWS, or an embedded operating system such as VxWorks) that includes procedures for handling various basic system services;
an electronic address 404 associated with the client device 300 that identifies the client device 300; and
a client application 420 that presents media to a user, such as a visualization of a digital representation of one or more data elements associated with an amount of strain captured at an exercise bar 100.

In some embodiments, an electronic address 418 is associated with the client device 300, which is utilized to at least uniquely identify the client device 300 from other devices and components of the distributed system 100.

In some embodiments, a client application 320 is a group of instructions that, when executed by a processor, generates content for presentation to the user, such as a user interface for presenting a digital representation of a set of data elements obtained from the exercise bar 100 (e.g., user interface 1500 of FIG. 15, user interface 1600 of FIG. 16, user interface 1700 of FIG. 17, user interface 1800 of FIG. 18). In some embodiments, the client application 320 generates content in response to inputs received from the user through the client device 300, such as the inputs 480 of the client device.

Each of the above identified modules and applications correspond to a set of executable instructions for performing one or more functions described above and the methods described in the present disclosure (e.g., the computer-implemented methods and other information processing methods described herein, method 1100 of FIG. 11, method 1200 of FIG. 12, etc.). These modules (e.g., sets of instructions) need not be implemented as separate software programs, procedures or modules, and thus various subsets of these modules are, optionally, combined or otherwise re-arranged in various embodiments of the present disclosure. In some embodiments, the memory 492 optionally stores a subset of the modules and data structures identified above. Furthermore, in some embodiments, the memory 492 stores additional modules and data structures not described above.

It should be appreciated that the client device 300 of FIG. 4 is only one example of a client device 300, and that the client device 300 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Referring to FIGS. 4 through 10, an exercise bar 100 of the present disclosure is illustrated in accordance with various embodiments.

In some embodiments, the exercise bar 100 of the present disclosure has any of the features or elements of any of the exercise bars disclosed in United States Patent Publication no.: 2020/0269080 A1, entitled "Variable Resistance Exercise Device," filed Feb. 22, 2019, which is hereby incorporated by reference in its entirety for all purposes.

Figure 6:
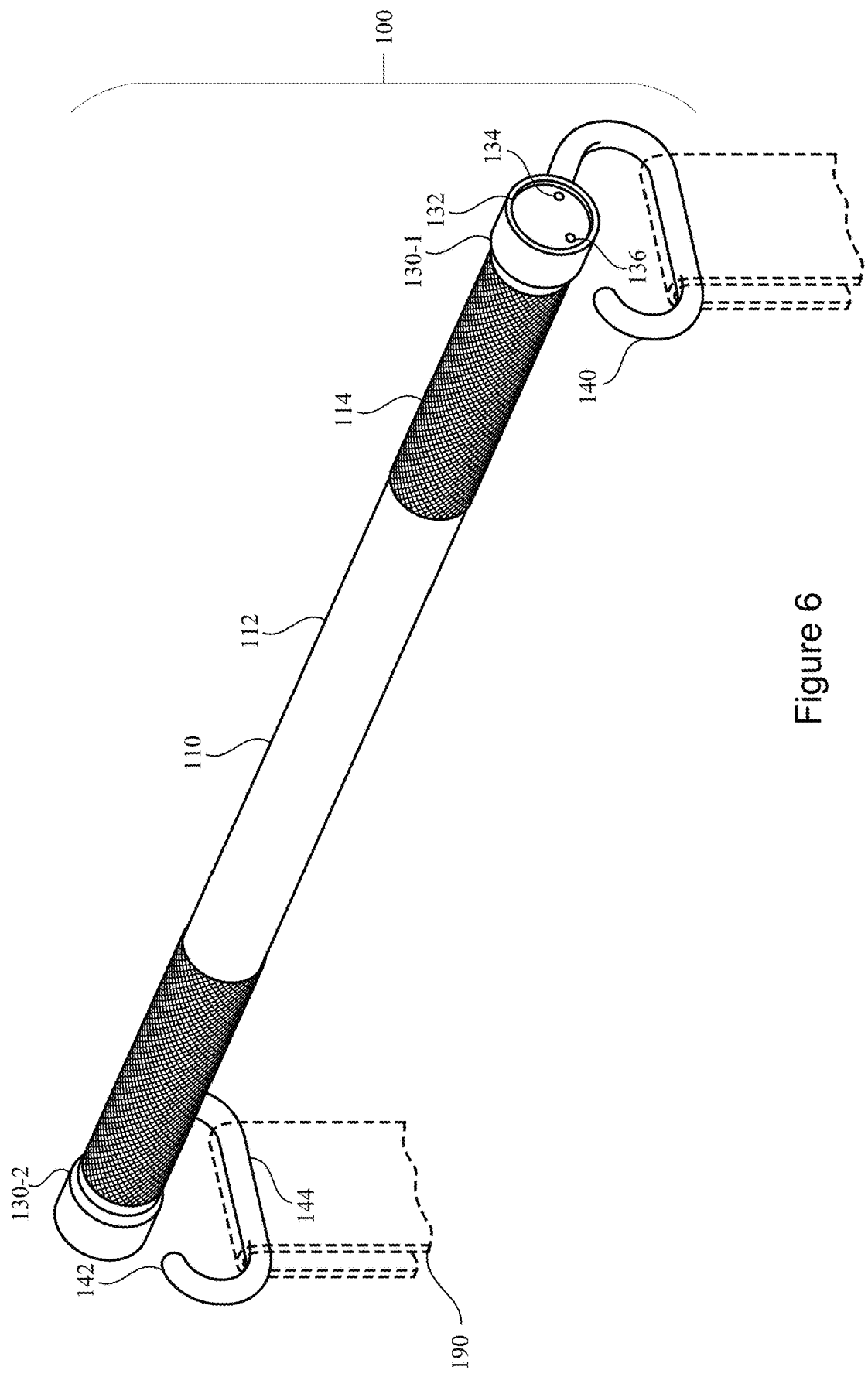
FIG. 6 illustrates an exemplary exercise bar, in accordance with an embodiment of the present disclosure.
Figure 7:
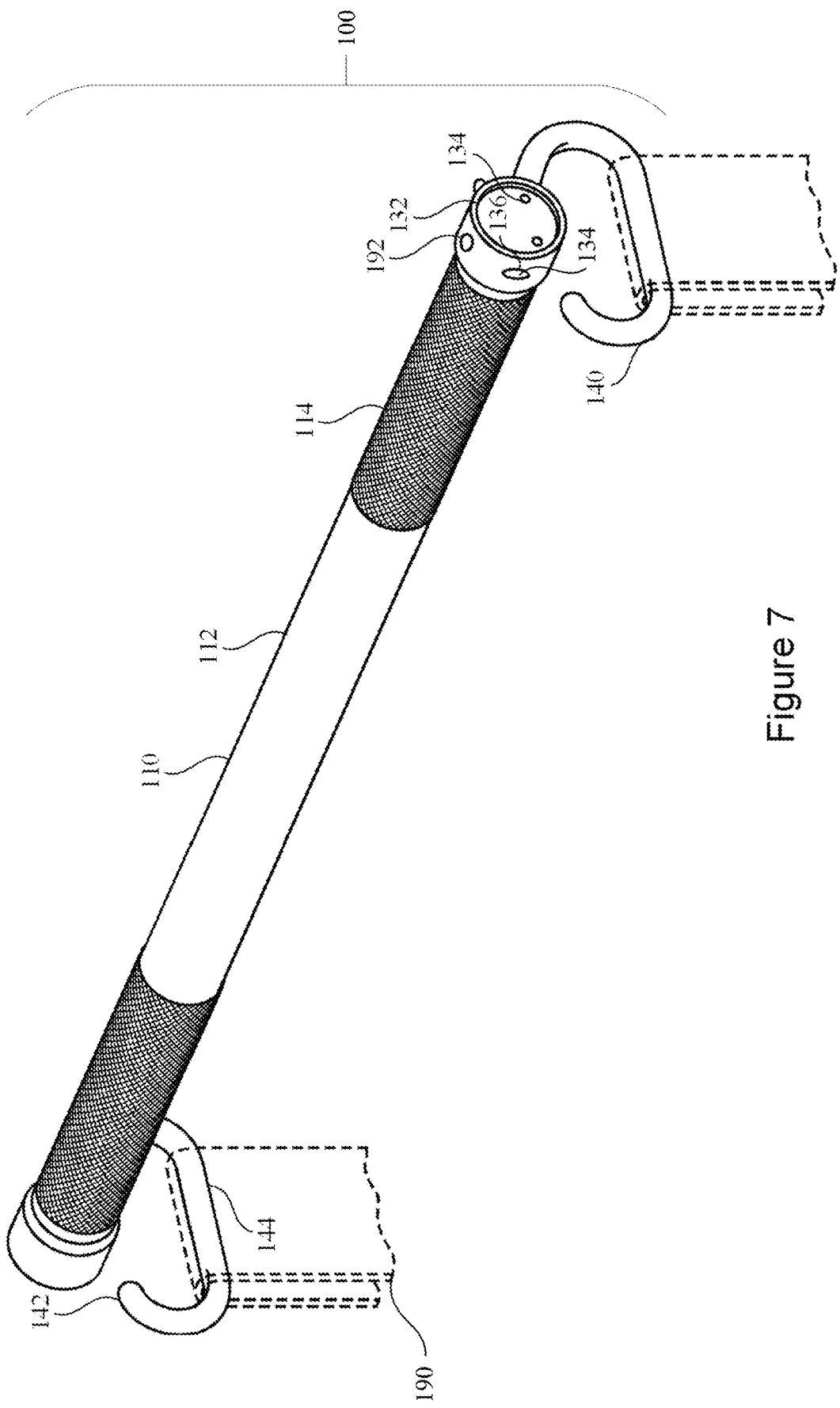
FIG. 7 illustrates another exemplary exercise bar, in accordance with an embodiment of the present disclosure.

In some embodiments, the exercise bar 100 includes a handle tube 110 that is configured to accommodate hands of an end-user (e.g., end-user 610 of FIGS. 6 and 7). The handle tube includes a first end (e.g., first end 111a of FIG. 8A) and a second end (e.g., second end 111b of FIG. 8A) that opposes the first end portion.

In some embodiments, the handle tube 110 is between about 40 centimeters (cm) and about 80 cm in length. In some embodiments, the handle tube 110 is between 50 cm and 300 cm in length. In some embodiments, the handle tube 110 is between 100 cm and 250 cm in length. In some embodiments, the handle tube 110 is between 150 cm and 230 cm in length.

In some embodiments, the handle tube 110 is about 220 cm in length (e.g., approximately a length of an Olympic barbell).

In some embodiments, the handle tube 110 is at least 40 cm, at least 60 cm, at least 80 cm, at least 100 cm, at least 120 cm, at least 140 cm, at least 160 cm, at least 180 cm, at least 200 cm, at least 220 cm, at least 240 cm, at least 260 cm, at least 280 cm, or at least 300 cm. In some embodiments, the handle tube 110 is at most 40 cm, at most 60 cm, at most 80 cm, at most 100 cm, at most 120 cm, at most 140 cm, at most 160 cm, at most 180 cm, at most 200 cm, at most 220 cm, at most 240 cm, at most 260 cm, at most 280 cm, or at most 300 cm.

Moreover, the handle tube 110 has a diameter of between about 3 centimeters and about 5 centimeters. In some particular embodiments the diameter of the handle tube 110 is 2.5 cm. In some embodiments, the diameter of the handle tube 110 is about 2.8 cm. In some embodiments, the diameter of the handle tube 110 is about 5 cm. In some embodiments, the diameter of the handle tube 110 is about 5.1 cm. In some embodiments, the diameter of the handle tube 110 is between 2.5 cm and 5.5 cm. In some embodiments, the diameter of the handle tube 110 is between 3.0 cm and 5.3 cm.

In some embodiments, the diameter of the handle tube 110 is at least 2.5 cm, at least 2.7 cm, at least 2.9 cm, at least 3.1 cm, at least 3.3 cm, at least 3.5 cm, at least 3.7 cm, at least 3.9 cm, at least 4.1 cm, at least 4.3 cm, at least 4.5 cm, at least 4.7 cm, at least 4.9 cm, or at least 5.1 cm. In some embodiments, the diameter of the handle tube 110 is at most 2.5 cm, at most 2.7 cm, at most 2.9 cm, at most 3.1 cm, at most 3.3 cm, at most 3.5 cm, at most 3.7 cm, at most 3.9 cm, at most 4.1 cm, at most 4.3 cm, at most 4.5 cm, at most 4.7 cm, at most 4.9 cm, or at most 5.1 cm.

In some embodiments, the handle tube 110 further includes a first circumferential grip region on an exterior circumferential surface of the handle tube. In some embodiments, the first circumferential grip region includes a midpoint of the exterior circumferential surface of the handle tube, which allows the user to comfortably grasp the exercise bar 100 with a narrow grip. Accordingly, when the handle tube 110 is used (e.g., grasped) by a user, a load applied to the exercise bar 110 is substantially symmetric about a midpoint of the handle tube 110.

For instance, in some embodiments the handle tube 110 includes a first circumferential grip region type 112 and a second circumferential grip region type 114. In some embodiments, the first circumferential grip region type 112 is a level (e.g., smooth) surface while the second circumferential grip region type 114 is characterized by a pattern of straight, angled, and/or crossed lines (e.g., a result of being subjected to knurling). In some embodiments, the handle tube 110 includes a first end portion and a second end portion (e.g., a right hand portion and a left hand portion). Accordingly, in some embodiments the second circumferential grip region type 114 is disposed at both the first end portion and the second end portion of the handle tube 110 while the first circumferential grip region is disposed on the handle tube 110 between the first and second end portions. Utilizing the circumferential grip regions at least improves the grip of an end-user while the user utilizes the exercise bar 100. In some embodiments the first and second end portions occupied by the second circumferential grip region type 114 are each between 10 cm and 30 cm in length. In some embodiments the first and second end portions occupied by the second circumferential grip region type 114 collectively occupy between 35 percent and 65 percent of the total length of the handle tube 110.

In some embodiments, the handle tube 110 is made of austenite steel (e.g., AISI type no. 201, 202, 301, 302, 302B, 303, 303 (Se), 304, 304L, 305, 308, 309, 309S, 310, 310S, 314, 316, 317, 321, 347, or 348, etc.), a martensitic steel (e.g., AISI type no. 403, 410, 414, 416, 416(Se), 420, 420F, 431, 440A, 440B, 440C, or 501, etc.), or a ferritic steel (AISI type no. 405, 429, 430, 430F, 430F(Se), 442, 446, or 502) such as those described in Table 6.2.18a of Marks' *Standard Handbook for Mechanical Engineers*, ninth edition, 1987, McGraw-Hill, Inc., at p. 6-37 purposes. In some embodiments, the handle tube 110 is made of a nickel alloy (e.g., Nickel 270, Nickel 200, Duranickel 301, Monel 400, Monel K-500, Hastelloy C, Incoloy 825, Inconel 600, Inconel 718, or TD Ni) such as those described in Table 6.4.7 of Marks' *Standard Handbook for Mechanical Engineers*, ninth edition, 1987, McGraw-Hill, Inc., at p. 6.72, which is hereby incorporated by reference for all purposes. In some embodiments handle tube 110 is made of a high-strength low-alloy steel (HSLA). HSLA is a type of alloy steel that provides better mechanical properties or greater resistance to corrosion than carbon steel. In some embodiments the HSLA steel has a carbon content between 0.05-0.25%. In some embodiments the HSLA steel includes up to 2.0% manganese and small quantities of copper, nickel, niobium, nitrogen, vanadium, chromium, molybdenum, titanium, calcium, rare earth elements, or zirconium. For more disclosure on HSLA steel that can be used to make the handle tube 100, see Degarmo et al., 2003, *Materials and Processes in Manufacturing* (9th ed.), Wiley, ISBN 0-471-65653-4, and Oberg et al., 1996, *Machinery's Handbook* (25th ed.), Industrial Press Inc., each of which is hereby incorporated by reference.

Utilizing metal typically increases a load bearing capacity of the exercise bar 100. However, the present disclosure is not limited thereto. For instance, in some embodiments all or a portion of the handle tube 110 is coated with an elastomer (e.g., a rubberized coating). Moreover, in some embodiments the handle tube 110 includes a grip disposed about a circumference thereof (e.g., a foam grip and/or a rubber grip, etc.). In some such embodiments, the handle tube 110 includes one or more circumferential grip region types. For instance, in some embodiments the handle tube includes a first circumferential grip region type 112 and a second circumferential grip region type 114. In some embodiments, the first circumferential grip region type 112 is a level (e.g., smooth) uncoated surface while the second circumferential grip region type 114 is coated with an elastomer or a foam. In some embodiments, the handle tube 110 includes a first end portion and a second end portion (e.g., a right hand portion and a left hand portion). Accordingly, in some such embodiments the second circumferential grip region type 114 is disposed at both the first end portion and the second end portion of the handle tube 110 while the first circumferential grip region is disposed on the handle tube 110 between the first and second end portions. Utilizing the circumferential grip regions at least improves the grip of an end-user while the user utilizes the exercise bar 100. In some embodiments, the second circumferential grip region type 114 is coated with GR-S, neoprene, a nitrile rubber, a butyl rubber, a polysulfide rubber, or an ethylene-propylene rubber (e.g., ethylene propylene diene methylene (EPDM) rubber), a cyclized rubber (e.g., Thermoprene). See, for example, Sections 6-161 through 6-163 of Marks' *Standard*

*Handbook for Mechanical Engineers*, ninth edition, 1987, McGraw-Hill, Inc., beginning at p. 6.161, which is hereby incorporated by reference.

In some embodiments, the handle tube 110 includes a longitudinal interior bore (e.g., longitudinal interior bore 202 of FIG. 8A). In some such embodiments, the longitudinal interior bore 202 is aligned, or substantially aligned, with a third longitudinal axis of the handle tube 110.

A center shaft (e.g., center shaft 150 of FIG. 8A) of the exercise bar 110 includes an outer surface. Accordingly, the center shaft 150 is fitted through the longitudinal interior bore 202 of the handle tube 110, which exposes the outer surface of the center shaft 150 towards an interior surface of the longitudinal interior bore 202. In some embodiments, this creates a gap or cushion between the outer surface of the center shaft 150 and the interior surface of the longitudinal interior bore 202. Furthermore, a first end portion (e.g., end portion 302a of FIG. 8A) of the center shaft 150 is exposed at the first end of the handle tube 110 and a second end portion (e.g., end portion 308b of FIG. 8A) of the center shaft 150 at the second end of the handle tube 110. Accordingly, in such embodiments, the first end portion 302a of the center shaft 150 and/or the second end portion 302b of the center shaft 150 is configured to receive a load (e.g., from an elastic band or a weight plate). In some embodiments, the center shaft 150 is fitted through the handle tube 110 such that a first longitudinal axis of the center shaft 150 is configured to intersect the third longitudinal axis of the handle tube 110 along a length (e.g., some or all) of the exercise bar 100. Said otherwise, in some embodiments, a first origin of a first cross-sectional area of the handle 110 is the same as a second origin of a second cross sectional area of the center shaft 150.

In some embodiments, the center shaft 150 is a hollow center shaft, which that the center shaft 150 is spatially defined, at least in part, by a wall thickness based on an inner diameter of the center shaft 150 and an outer diameter of the center shaft 150. In some embodiments, as the hollow center shaft, the first end portion 302a and/or the second end portion 302b of the center shaft 150 is open, which exposes an interior of the center shaft 150. From this, the interior of the center shaft 150 is configured to accommodate one or more cables or wires, which facilitate providing physical electronic communication between two or more components of the exercise bar 100, such as the sensor 180 and the processor 272. However, the present disclosure is not limited thereto.

As described supra, in some embodiments, the center shaft 150 is configured to receive a load. From this, a load path is formed from the load through the center shaft 150, which bypasses the handle tube 110. Accordingly, the center shaft 150 is configured to longitudinally rotates independent of the handle tube 110. For instance, in some embodiments, the exercise bar 100 includes a respective handle bearing (e.g., bearing 152 of FIG. 8A) for each end portion 302 of the exercise bar 110. Each handle bearing 152 includes a respective hollowed cylindrical piece that includes an inner circumferential surface and an outer circumferential surface (e.g., an inner diameter and an outer diameter). In some embodiments, each handle bearing 152 is a bushing. In some embodiments, each end portion 302 of the center shaft 150 is fitted through the respective cylindrical piece of the handle bearing 152, with the exterior circumferential surface of the respective cylindrical piece of the handle bearing 152 contacting, in turn, the inner circumferential surface of center shaft 150 as illustrated, for example, in FIG. 3. In some embodiments, the handle bearing 152 includes a ball, needle, roller, or other bearing mechanism. Additionally, the longitudinal interior bore 202 of the handle tube 110 encapsulates and makes frictional contact with the outer surface of each handle bearing 152, as illustrated in FIG. 9. This frictional contact with the handle bearings 152 allows for the handle tube 110 to rotate independent from the handle end the center shaft 150, which improves at least a range of motion and/or a number of exercises capable of being performed by the bar exercise 100. Furthermore, this allows for a load path through the center shaft 150 to bypass the handle tube 110 substantially or completely.

Figure 8B:
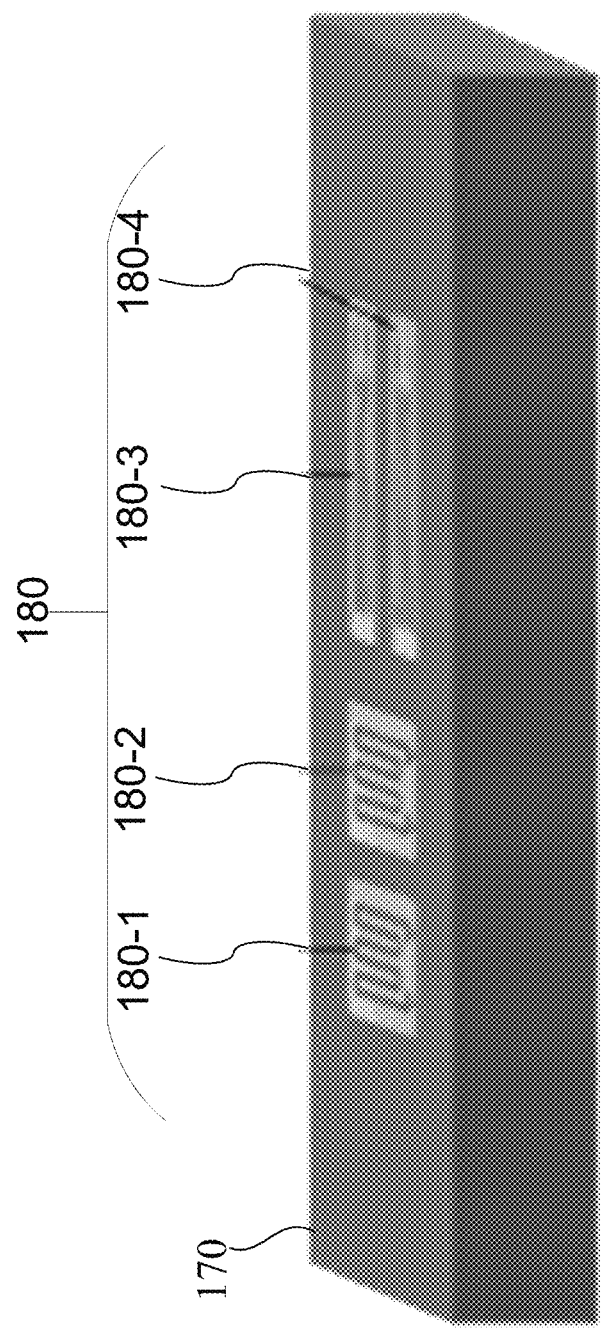
FIG. 8B is an enlarged view of a mounting section.
Figure 8C:
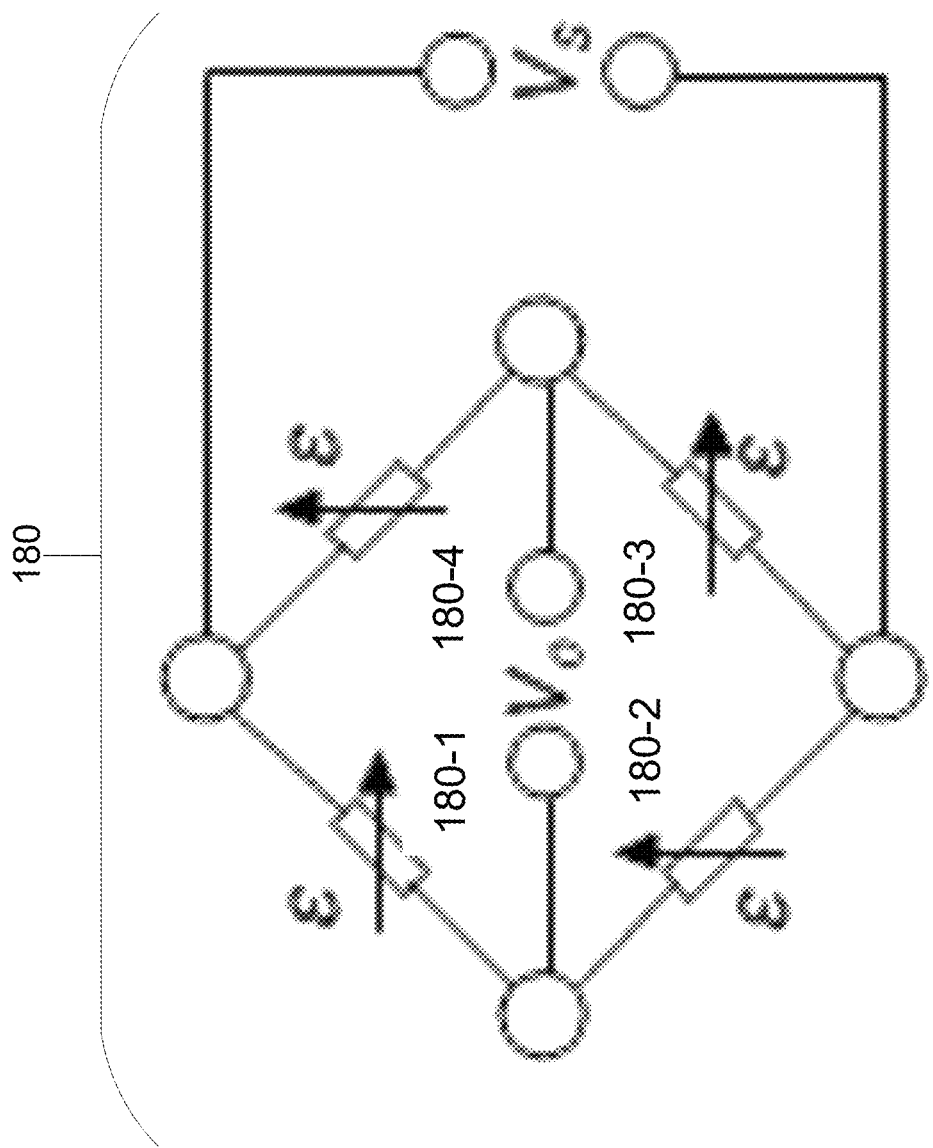
FIG. 8C is a schematic view of an exemplary sensor of an exercise bar, in accordance with an embodiment of the present disclosure.
Figure 9:
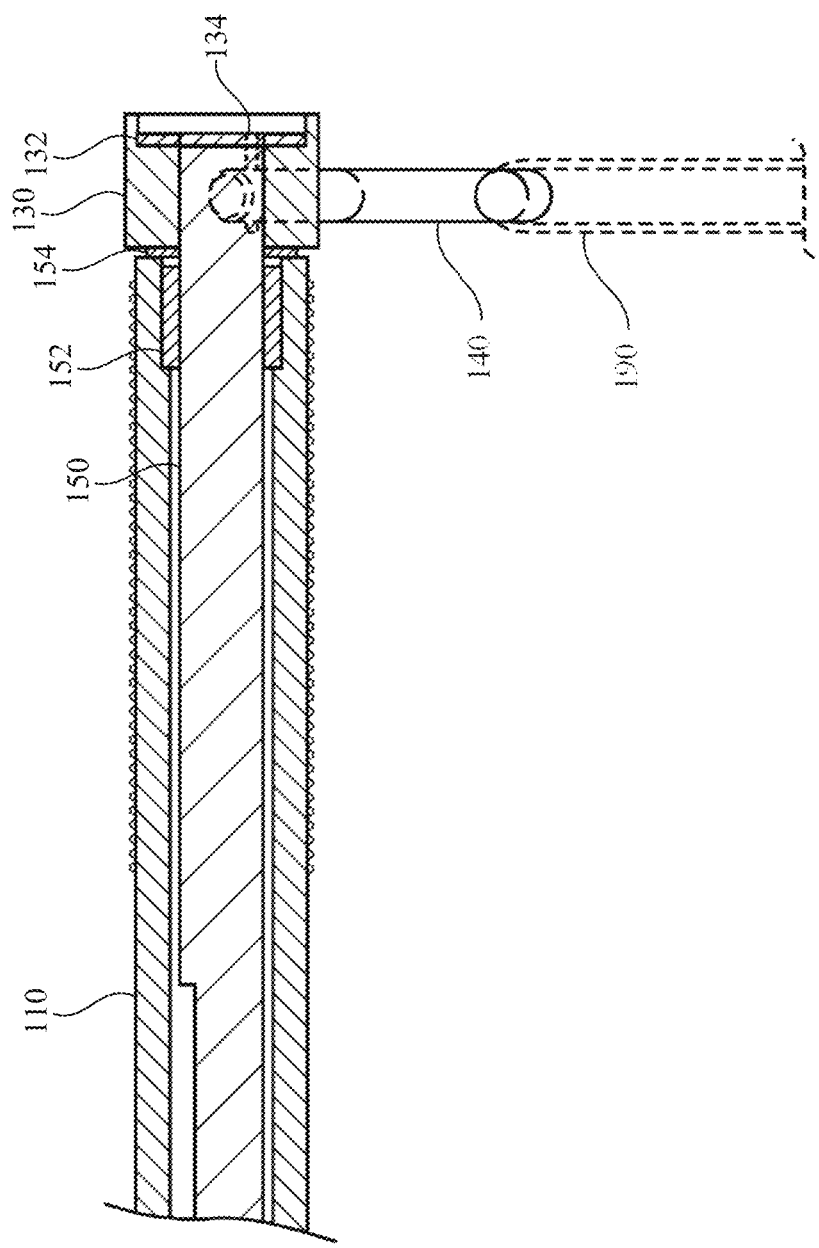
FIG. 9 illustrates a cross sectional view of an exemplary exercise bar, in accordance with an embodiment of the present disclosure.

Referring briefly to FIGS. 8B and 8C, the exercise bar 100 includes a sensor (e.g., sensor 180 of FIG. 8B). In some embodiments, the sensor 180 is configured to measure a mechanical quantity, or property, of the exercise bar including a force applied to the exercise bar 100, such as a force applied by one or more weight plates and/or an exercise band disposed on the exercise bar 100. In this way, in some such embodiments, the sensor 180 is configured to measure a strain applied to the center shaft 150 that is caused through the exercise bar 100 by gravity, such as a strain gauge. Accordingly, in some embodiments, the sensor 180 includes a strain sensor that measures a spatial deformation in the exercise bar 100 that causes the strain sensor 180 to experience a change in electrical load, such as resistance, that is proportional to the spatial deformation. A non-limiting example of the strain sensor 180 includes a foil strain gauge, a plurality of shear strain gauges (e.g., four shear strain gauges).

In some embodiments, the sensor 180 includes a Wheatstone bridge sensor 180 that is a configuration of four strain sensors in a complete network. For instance, in some embodiments, the four strain sensors of the Wheatstone bridge sensor 180 have a gauge value in a range from about from about $1*10^{-4}$ Ohms ($\Omega$) to about $1*10^{-2}\Omega$, from about $1*10^{-4}\Omega$ to about $1*10^{-1}\Omega$, from about $1*10^{-4}$ Ohms ($\Omega$) to about $100\Omega$, from about $50\Omega$ to about $300\Omega$ (e.g., about $120\Omega$), from about $200\Omega$ to about $400\Omega$ (e.g., about $350\Omega$), from about $300\Omega$ to about $500\Omega$, from about $400\Omega$ to about $750\Omega$, from about 500 to about $2*10^{3}\Omega$ (e.g., about 1 k$\Omega$).

In some embodiments, the Wheatstone bridge sensor is a balanced Wheatstone bridge sensor. As a balanced Wheatstone bridge sensor, a protentional difference between two midpoints of the network is zero, such that the resistance in a first leg of the Wheatstone bridge sensor 180 is equal to a second leg of the Wheatstone bridge sensor 180. In some embodiments, the Wheatstone bridge sensor is a full Wheatstone bridge sensor, which is configured to measure the amount of the strain on the exercise bar when the exercise bar 100 is under tension and/or compression. As the full Wheatstone bridge sensor 180, four strain sensors (e.g., first strain sensor 180-1, second strain sensor 180-2, third strain sensor 180-3, fourth strain sensor 180-4 of FIG. 8B) are disposed on a surface of the exercise bar 100, such as the mounting section 170, as a full bridge, which allows for excellent compensation of temperature effects experienced by the sensor 180. Furthermore, the full Wheatstone bridge sensor 180 provides excellent common mode rejection (CMR) in order to suppress a signal (e.g., noise) that is common to two or more inputs (e.g., the first leg and the second leg of the sensor 180).

As illustrated by FIGS. 8A and 8B, in some embodiments, the first longitudinal axis of the center shaft 150 is parallel to a second longitudinal axis of the sensor 180. From this, the exercise bar 100 allows for providing a Wheatstone bridge effect, in which two of the strain sensors 180 (e.g., third strain sensor 180-3 and fourth strain sensor 180-4 of FIG. 8B) are aligned with the first longitudinal axis of the center shaft 150. As such, the two strain sensors 180 have the corresponding conductive substrate of a respective strain sensor 180 maximally deformed when an amount of strain is applied along the first longitudinal axis of the center shaft. On the other hand, the remaining strain sensors 180 (e.g., first strain sensor 180-1 and second strain sensor 180-2 of FIG. 8B) are relatively unimpeded, providing for a variance in voltage across the Wheatstone bridge sensor 180 that is proportional to the amount of strain induced in the center shaft 150 when the exercise bar 100 is utilized by an end-user and has a load applied through the exercise bar 100. In some embodiments, a direction of an arrow associated with each respective strain sensor 180 of FIG. 8C denotes an active strain gauge. However, the present disclosure is not limited thereto.

Additional details and information regarding the strain sensor and the Wheatstone bridge sensor 180 of the exercise bar 100 can be found at Stefanescu, D, 2011, "Strain Gauges and Wheatstone Bridges—Basic Instrumentation and New Applications for Electrical Measurement of Non-Electrical Quantities," Eighth International Multi-Conference on Systems, Signals and Devices, IEEE, pg. 1, each of which is hereby incorporated by reference in its entirety.

This sensor 180 of the exercise bar 100 is disposed on a mounting section 170 of the outer surface of the center shaft 150. For instance, in some such embodiments, the mounting section 170 is recessed into the center shaft 150 by a first depth. By having the mounting section 170 recessed into the center shaft 150 by the first depth, the sensor 180 is at least protected from physical damage to the exercise bar, such as denting of the handle tube 100. In some embodiments, the first depth is from about 0.25 mm to about 10 mm, from about 0.5 mm to about 7.5 mm, from about 1 mm to about 5 mm, or about 2.5 mm (e.g., 3.2 mm). This mounting section 170 is configured to provide a flat surface to accommodate a portion (e.g., some or all) of the sensor 180. As used herein, the term "flat" means a surface or face at which every point is perpendicular to the direction that gravity acts. As such, in some embodiments, the mounting section 170 includes a portion of the outer surface of the center shaft 150 that is flat surface. This flat surface of the mounting section 170 has spatial dimensions that are configured to accommodate the sensor 180. In this way, a first surface area of the mounting section 170 is greater than or equal to a second surface area of the sensor 180, which ensures that the sensor 180 is accommodated by the center 150 without interference from the handle tube 110.

From this, the mounting section 170 reduces errors when obtaining one or more measurements associated with a state of the exercise bar (e.g., an amount of strain applied to the exercise bar 100) by way of the sensor 180, such as interference cause by torsion applied to the exercise bar 100.

In some embodiments, the mounting section 170 includes a lateral bore (e.g., lateral bore 156 of FIG. 8A). This lateral bore 156 is configured to exposes an interior of the hollow center shaft 150. Furthermore, the lateral bore 156 is configured to have a diameter greater than a diameter of the wire or cable. From this, the interior of the hollow center shaft 150 allows for physical electronic communication between the sensor 180 and a processor 272 of the exercise bar 100 (e.g., CPU 272 of exercise bar 100 of FIG. 2A).

In some embodiments, the mounting section 170 is at a midpoint of the center shaft 150, which allows for a balanced tensile load to be applied to the sensor 180.

Furthermore, the exercise bar 100 includes a processor 272 that is disposed in an interior of the exercise bar 150, such as an interior of the center shaft 150, an interior portion of the handle tube 110, and the like. Accordingly, the sensor 180 is in electronic communication with the processor 272 in the exercise bar 100, which allows for the processor evaluate one or more data elements captured by the sensor 180 (e.g., measured voltages associated with a strain applied to the sensor 180) and arrive at a determination of a result, such as an amount of strain applied to the exercise bar 100.

In some embodiments, the processor 272 is an integrated circuit. In some embodiments, the integrated circuit 272 includes a transmitter (e.g., transceiver 298 of FIG. 2A) that allow the exercise bar 100 to communicate information obtained by the sensor 180 through a communication network 180. In some embodiments, the integrated circuit 272 includes a receiver (e.g., transceiver 298 of FIG. 2A) that allows the exercise bar 100 to receive one or more instructions through the communication network 106, such as a first instruction to change a state of a sensory output mechanism 190 of the exercise bar 100. Accordingly, in some such embodiments, the integrated circuit 272 includes a transceiver (e.g., transceiver 298 of FIG. 2A), which allows the exercise bar 100 to both transmit and receive information to and/or from an exercise system 200, a client device 300, or both through the communication network 106. In some embodiments, the integrated circuit 272 is an application specific integrated circuit. As the application specific integrated circuit 272, the processor 272 of the exercise bar 100 is configured, at least in part, to control one or more sensor output mechanisms of the exercise bar 100, such as a light source of the exercise bar 100.

Figure 10:
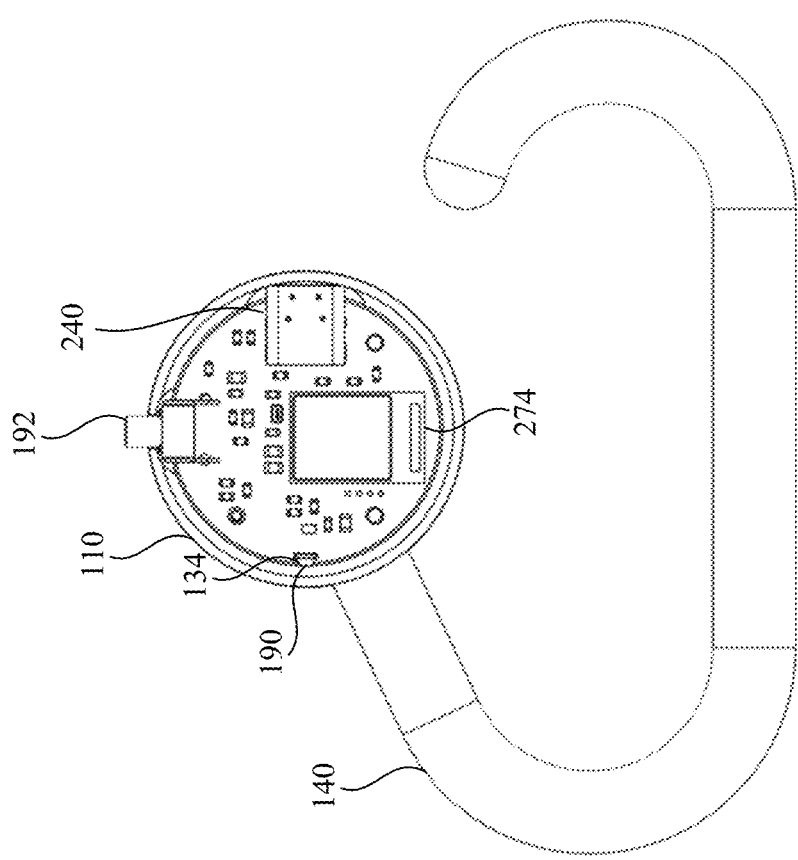
FIG. 10 illustrates an exemplary circuit board of an exercise bar, in accordance with an embodiment of the present disclosure.

In some embodiments, the exercise bar 100 further includes a switch mechanism (e.g., switch mechanism 192 of FIG. 8A, switch mechanism 192 of FIG. 10, etc.). The switch mechanism 192 is configured to interpose between the sensor 180 and the processor 272 of the exercise bar 100, such as by separating the sensor 180 and the processor 272 through one or more circuit logics. Accordingly, the switch mechanism 192 is configured to interrupt the electronic communication between the sensor 180 and the processor 272 of the exercise bar 100. In this way, the switch mechanism 192 provides analog control to the end-user over a state of the exercise bar 100. For instance, in some embodiments, the switch mechanism 192 is configured, for example, to power on the exercise bar 100 through a power supply 240, power off the exercise bar 100, or reset a memory 292 of the exercise bar 100. However, the present disclosure is not limited thereto.

In some embodiments, the exercise bar 100 further includes a first end cap (e.g., first end cap 130-1 of FIG. 6) fixedly disposed about the first end of the handle tube 110 or the first end portion 302a of the center shaft 150. In some embodiments, an interior portion of the first end cap is configured to accommodate the processor 272. In some embodiments, the first end cap is fixedly disposed about the first end portion of the center shaft 150. The first end cap longitudinally rotates independent of the handle tube 110.

In some embodiments, the exercise bar 100 further includes a second end cap (e.g., second end cap 130-2 of FIG. 6) fixedly disposed about the second end of the handle tube 110 or the second end portion 308b of the center shaft 150. In some embodiments, the second end cap is configured to accommodate a battery (e.g., power supply 240 of FIG. 4) configured to provide power to at least the processor 272.

In some embodiments, the exercise bar 100 includes a sensory output mechanism 190 that is configured to provide a sensory output sensed by a user of the exercise bar 100. For instance, in some embodiments, the sensory output mechanism 190 includes a light source (e.g., light source sensory output mechanism), a vibration source (e.g., vibration sensory output mechanism), an audio source (e.g., audio sensory output mechanism), or a combination thereof. Accordingly, in some embodiments, the sensory output mechanism 190 is housed by the exercise bar 100, such as by interfacing with an interior surface of the handle tube 110. However, the present disclosure is not limited thereto.

In some embodiments, an exterior circumferential surface of the first end cap 130-1 includes a first bore (e.g., first bore 303a of FIG. 8A) configured to accommodate a light source in electronic communication with the processor. In such embodiments, the light source is a sensory output mechanism 190 that is configured to provide visual sensory output for perception by the end-user of the exercise bar 100. In some embodiments, the exterior circumferential surface of the handle tube 110 further includes a first bore (e.g., first bore 136 of FIG. 8A) that is configured to accommodate the light source 190. For instance, in some such embodiments, a first end portion of the first bore 136 includes an aperture (e.g., aperture 134 of FIG. 7) configured to accommodate the light source 190, which exposes an interior of the first bore.

From this, light emitted by the light source 190 is unimpeded by way of the first bore of the handle tube 110.

In some embodiments, the light source 190 is a light emitting diode (LED). In some embodiments, the light source 190 includes one or more stable LEDs, one or more tunable LEDs, or a combination thereof. In some embodiments, the light source includes one or more light sources that vary in wavelength with time or a predetermined function.

Figure 5:
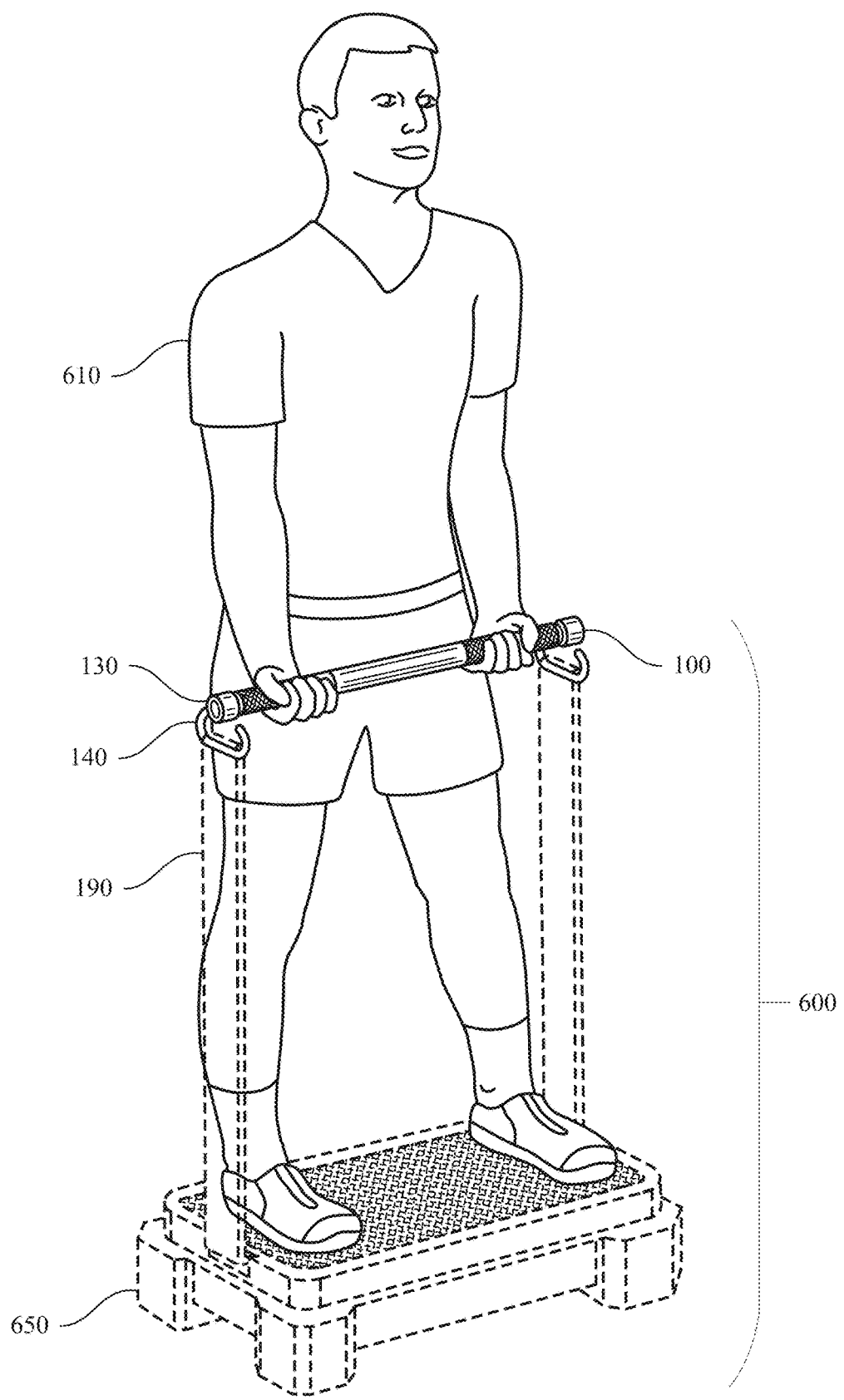
FIG. 5 illustrates an end-user utilizing an exemplary exercise bar in a first position, in accordance with an embodiment of the present disclosure.

In some embodiments, the exercise bar 100 further includes a first band arm (e.g., band arm 140 of FIG. 5, band arm 140 of FIG. 6, band arm 140 of FIG. 7, band arm 140 of FIG. 8A, band arm 140 of FIG. 9, band arm 140 of FIG. 10, etc.). In some embodiments, the first band arm 140 is fitted onto the first end of the center shaft 150. Additionally, the exercise bar 100 includes a second band arm (e.g., band arm 142 of FIG. 6, band arm 140 of FIG. 7, etc.) fitted onto the second end of the center shaft 150. In some embodiments, the first band arm and the second band arm are fitted on the same surface of the exercise bar 100, such as on the same side of the exercise bar 100. In some embodiments, the first band arm and the second band arm are fitted on a curved surface of the exercise bar 100.

Now that a general exercise bar 100 has been described in accordance with various embodiments of the present disclosures, details regarding some processes in accordance with FIGS. 11 and 12 will be described. FIGS. 11 and 12 illustrates a flow chart of methods (e.g., method 1100 of FIG. 11, method 1200 of FIG. 12) for displaying exercise information, such as by communicating one or more instructions for controlling a sensory output mechanism 190 of an exercise bar 100 or displaying a representation of a set of data elements on a display.

Referring to FIG. 11, an exemplary method 1100 for providing sensory feedback an exercise bar 100, such as by controlling a sensory output mechanism 190 of the exercise bar 100 is provided, in accordance with some embodiments of the present disclosure. In the flow charts, the preferred parts of the methods are shown in solid line boxes, whereas optional variants of the methods, or optional equipment used by the methods, are shown in dashed line boxes.

Various modules in the memory 292 of the exercise bar 100, the memory 392 of the exercise system 200, the memory 492 of a client device 300, or a combination thereof perform certain processes of the method 1100 described in FIG. 11, unless expressly stated otherwise. Furthermore, it will be appreciated that the processes in FIG. 11 can be encoded in a single module or any combination of modules.

Block 1102. Referring to block 1102 of FIG. 11 a method 1100 for controlling a sensory output mechanism (e.g., sensory output mechanism 190 of FIG. 8A, sensory output mechanism 190 of FIG. 10, etc.), such that sensory feedback is provided at an exercise bar 100 for a user of the exercise bar 100. For instance, in some embodiments, the method 1100 allows for displaying exercise information at the exercise bar (e.g., exercise bar 100 of FIGS. 2A and 2B, exercise bar 100 of FIG. 8A, etc.). In such embodiments, the exercise information is associated with a mechanical quantity of the exercise bar 100, such as an amount of strain applied to the exercise bar 100. However, the present disclosure is not limited thereto. For instance, in some embodiments, the method 1100 allows for providing one or more sensory cue, which causes the user operating the exercise bar 100 to sense a change in a respective state of the sensory output mechanism 190.

Block 1104. Referring to block 1104, the method 1100 includes offsetting a longitudinal axis of a center shaft 150 of the exercise bar 100, which, due to a rigidity of the exercise bar 100, offsets all of the exercise bar 100. In some embodiments, this offsetting of the longitudinal axis of the center shaft 150 is provided by the end-user of the exercise bar 100. As a non-limiting example, consider the end-user vertically displacing the exercise bar 100 (e.g., lifting the exercise bar 100) during a bench press exercise 214, which offsets the longitudinal axis of the center shaft 150 when the end-user raises and lowers their arms. Accordingly, in such embodiments, the offsetting of the longitudinal axis of the center shaft 150 occurs during a phase of the exercise, such as an eccentric phase or a concentric phase of the exercise 214.

Block 1106. Referring to block 1106, the method 1100 includes determining an amount of strain of the exercise bar 100. This determining is performed when offsetting of the longitudinal axis of the center shaft (e.g., block 1104 of FIG. 11) by a processor of the exercise bar 100 (e.g., CPU 272 of FIG. 2A). Accordingly, in some such embodiments, the amount of the strain of the exercise bar 100 determined by the method 1100 is the strain when offsetting the longitudinal axis of the center shaft 150 of the exercise bar 100.

In some such embodiments, the strain is tensile. For instance, in some embodiments, the amount of strain of the exercise bar 100 is an effective strain at a point of measurement, such as point associated with the sensor 180 and/or the mounting section 170 of the exercise bar 100, which includes the midpoint of the center shaft 150. The effective strain (E) at a point of measurement is a function of a normal strain of the exercise bar 100 (E n) and a bending strain of the exercise bar 100 (E b). Said otherwise, in some such embodiments, the amount of effective strain of the exercise bar is, in some embodiments, determined by:

$$\varepsilon = \varepsilon_n + \varepsilon_b = \frac{1}{2(1+v)} * \frac{4}{k} * \frac{V_0}{V_s}$$

where $V_s$ is a supply voltage of the sensor 180, V 0 is an output voltage of the sensor 180, k is the k-factor of the sensor 180, and v is Poisson's ratio of the center shaft 150.

Block 1108. Referring to block 1108, the method 1100 includes communicating, by the processor 272, one or more instructions for causing a controller (e.g., sensory control module 220 of FIG. 2B) to cause a change in a respective state of a sensory output mechanism 190 of the exercise bar 100. In some embodiments, the one or more instructions is generated by the sensor control module 220 of the exercise bar 100. The one or more instructions is based on the determined amount of the strain that is applied through the exercise bar 100 during the offsetting of the longitudinal axis of the center shaft 150. For instance, in some such embodiments, the change in the respective state is from an ON a power state of the sensory output mechanism 190 to an OFF state. In some embodiments, the one or more instructions is generated in accordance with the offsetting of the longitudinal axis satisfying one or more threshold conditions 218, such as a threshold minimum displacement of the longitudinal axis or a threshold minimum strain applied to the center shaft 150. Accordingly, the method 1100 allows for sensory feedback to be provided to the user through the exercise bar 100 based on the offsetting of the longitudinal axis of the center shaft. From this, the end-user is provided with an improved exercise experience since the sensory feedback allows the end-user to enhance a future performance of the exercise based on the sensory feedback of a prior exercise. For instance, when performing the exercise, if the end-user fails to activate the sensory feedback mechanism when offsetting the longitudinal axis of the exercise bar 100, the end-user knows that the distance offset by the longitudinal axis fails to satisfy the one or more threshold conditions 218 for generating the one or more instructions.

Block 1110. Referring to block 1110, in some embodiments, the method 1100 further includes repeating the offsetting the longitudinal axis of the center shaft (e.g., block 1104 of FIG. 11), the determining the amount of the strain (e.g., block 1106 of FIG. 11), and the communicating one or more instructions (e.g., block 1108 of FIG. 11). From this, in some embodiments, the method 1100 dynamically updates a digital representation responsive to the aforementioned repeating. Said otherwise, in some embodiments, the method 1100 dynamically updates a digital representation responsive to the end-user of the exercise bar 100 performing a repetition of the exercise 214.

In some embodiments, the communicating further includes communicating, by a communications network (e.g., communication network 106 of FIG. 1), to a remote device (e.g., client device 300 of FIG. 4) a plurality of data elements. The plurality of data elements is obtained or derived (e.g., processed by the processor 272) from the sensor 180 of the exercise bar 100 during the offsetting of the longitudinal axis of the center shaft 150. In this way, the remote device is able to evaluate and store the plurality of data elements remote from the exercise bar 100, which reduces a need for increased memory at the exercise bar 100.

In some embodiments, the plurality of data elements includes a maximum data element in the plurality of data elements. For instance, in some embodiments, the maximum data element is a maximum force measured by the sensor 180, such as a maximum tensile strain applied to the center shaft 150. In some embodiments, the maximum data element in the plurality of data elements is a maximum period of time, such as the maximum period of time when performing a respective exercise 214 or a repetition of the respective exercise 214. In this way, in some embodiments, the plurality of data elements includes a period of time associated with the plurality of data elements. In some embodiments, the period of time associated with the plurality of data elements includes a first period of time of the offsetting the longitudinal axis of the center shaft with a phase of the offsetting the longitudinal axis of the center shaft or an average period of time associated with the phase of the offsetting the longitudinal axis of the center shaft 150. Furthermore, in some embodiments, the phase of the offsetting the longitudinal axis of the center shaft is an eccentric phase, a concentric phase, an isometric phase, or a combination thereof.

In some embodiments, the communicating the one or more instructions further includes displaying, at the display 478 of the client device 300, a digital representation of the plurality of data elements (e.g., digital representation 1000 of FIG. 15, digital representation 1000 of FIG. 18, method 1200 of FIG. 12, etc.). In some embodiments, the digital representation includes a plurality of nodes and a plurality of edges, with each node associated with a set of one or more data elements in the plurality of data elements. However, the present disclosure is not limited thereto. In this way, in some embodiments, the digital representation 1000 includes a table, a chart, a graph, or a combination thereof that provides as visualization of the plurality of data elements that is obtained from the exercise bar 100. For instance, referring to FIG. 16, a user interface 1600 presents a digital representation 1000 that shows an effective strain on the center shaft 150 in real time as the user performs an overhead press exercise 214-4. More particularly, the user has performed three repetitions using an elastic band.

In some embodiments, the one or more instructions for changing the respective state of the sensory output mechanism 190 cause the sensory output mechanism 190 to fire, such as one or more control instructions generated from the sensory control module 220 of the exercise bar 100. By firing the sensory output mechanism 190, the sensory output mechanism provides an output, either mechanically (e.g., displacing a mass) or digitally (e.g., generating a signal), that is sensed by the user of the exercise bar 100, such as by seeing light provided by the sensory output mechanism 190, hearing audio provided by the sensory output mechanism 190, feeling output provided by the sensory output mechanism 190, or a combination thereof.

In some embodiments, the one or more instructions for firing the sensory output mechanism 190 includes, in accordance with a determination that each threshold condition in a first set of threshold conditions, in a plurality of threshold conditions, is satisfied, firing a first configuration of the sensory output mechanism 190. Furthermore, the one or more instructions for controlling the sensory output mechanism 190 includes, in accordance with a determination that each threshold condition in a second set of threshold conditions, in the plurality of threshold conditions, is satisfied, firing a second configuration of the sensory output mechanism 190. In some embodiments, a first threshold condition in the plurality of threshold conditions is associated with a threshold strain. In some embodiments, the first configuration of the sensory output mechanism 190 is an unpowered state, which ceases the sensory output mechanism 190 from providing an output. In this way, each respective configuration of the sensory output mechanism 190

In some embodiments, the first configuration is associated with a first frequency of firing the sensory output mechanism. In some such embodiments, the second configuration is associated with a second frequency of firing the sensory output mechanism, in which the second frequency is less than the first frequency. In some embodiments, the first frequency is in a range of from about 10 Hertz (Hz) to about 60 Hz. For instance, in some embodiments, the first frequency is 60 Hz and the second frequency is 10 Hz. However, the present disclosure is not limited thereto.

In some embodiments, the first frequency is and/or the second frequency is between 10 Hz and 60 Hz, between 10 Hz and 40 Hz, between 10 Hz and 20 Hz, between 20 Hz and 60 Hz, between 20 Hz and 40 Hz, between 30 Hz and 60 Hz, between 30 Hz and 40 Hz, between 40 Hz and 60 Hz, or between 50 Hz and 60 Hz. In some embodiments, the first frequency is and/or the second frequency is at least 10 Hz, at least 15 Hz, at least 20 Hz, at least 30 Hz, at least 40 Hz, at least 50 Hz, or at least 60 Hz. In some embodiments, the first frequency is and/or the second frequency is at most 10 Hz, at most 15 Hz, at most 20 Hz, at most 30 Hz, at most 40 Hz, at most 50 Hz, or at most 60 Hz.

In some embodiments, the frequency of the sensory output mechanism 190 is associated with a pulse provided by the sensory output mechanism, such as a number of cycles of providing the sensory feedback during a period of time. In some embodiments, a cycle is when the sensory output mechanism satisfies a threshold condition, such as a frequency is between 10 Hz and 60 Hz, or the like.

In some embodiments, the first configuration is associated with a first amplitude of firing the sensory output mechanism 190 and the second configuration is associated with a second amplitude of firing the sensory output mechanism less than the first amplitude. For instance, in some embodiments, the first amplitude is in a range of from about 0.5 millimeter (mm) to about 2.5 mm. In some embodiments, the first amplitude is between 0.5 mm and 2.5 mm, between 0.5 mm and 2 mm, between 0.5 mm and 1.5 mm, between 0.5 mm and 1 mm, between 1 mm and 2.5 mm, between 1 mm and 2 mm, between 1 mm and 1.5 mm, between 1.5 mm and 2.5 mm, between 1.5 mm and 2 mm, or 2 mm and 2.5 mm. In some embodiments, the first amplitude is at least 0.5 mm, at least 1 mm, at least 1.5 mm, at least 2 mm, or at least 2.5 mm. In some embodiments, the first amplitude is at most 0.5 mm, at most 1 mm, at most 1.5 mm, at most 2 mm, or at most 2.5 mm.

In some such embodiments, by using the first configuration and the second configuration with different amplitudes, the method 1100 provides unique sensory feedback to the user from the different amplitudes. For instance, in some embodiments, the first amplitude is greater than the second amplitude, which provides for a higher intensity of light, vibration, audio, or any combination thereof provided from the sensory output mechanism 190. However, the present disclosure is not limited thereto.

In some embodiments, the first configuration is associated with a first sequence of firing the sensory output mechanism and the second configuration is associated with a second sequence of firing the sensory output mechanism different from the first sequence. In some embodiments, the first sequence is a periodic sequence of firing the sensory output mechanism and the second sequence is a non-periodic sequence of firing the sensory output mechanism. In some embodiments, the period sequence is a recurring sequence, such as an ordered series of pulses of different amplitude. For instance, in some embodiments, the first sequence of firing the light source sensory output mechanism 190 includes providing three pulses of light within 5 seconds and the second sequence of firing the light source sensory output mechanism 190 includes providing ten pulses of light within 1 second. However, the present disclosure is not limited thereto.

In some embodiments, the first configuration is associated with a first audio waveform provided when firing the sensory output mechanism and the second configuration is associated with a second audio waveform when firing the sensory output mechanism different from the first audio waveform. In some such embodiments, by using the different audio wave forms, each respective configuration provides a unique audio cue to the user in order to aid and/or improve the user when performing exercises 214 with the exercise bar 100. However, the present disclosure is not limited thereto.

In this way, in some embodiments, the sensory output mechanism 190 includes an audio sensory output mechanism, a light source sensory output mechanism, a vibration sensory output mechanism, or a combination thereof.

In some embodiments, in a first state, the vibration sensory output mechanism 190 provides a plurality of vibrations through the center shaft 150 and/or the handle tube 110 of the exercise bar 100. In some embodiments, the plurality of vibrations provided by the vibration sensory output mechanism 190 is synchronous linear vibrations that is propagated in a first axis that is parallel to a lateral axis of the exercise bar 100. In some embodiments, in a second state, the sensory output mechanism 190 is turned OFF. Accordingly, in some embodiments, the sensory output mechanism 190 includes one or more light output mechanisms, one or more vibration output mechanisms, one or more audio output mechanisms, or a combination thereof.

In some embodiments, the offsetting includes a vertical displacement of the longitudinal axis, such a distance between an initial height if the exercise bar 100 and an instantaneous height (e.g., second height) of the exercise bar 100 or a maximum height of the exercise bar 100. In some embodiments, the vertical displacement is defined by a range of motion associated with performing a respective exercise, such as a range of motion associated with a squat, a bench press, a curl, or the like.

Now that a method for controlling a sensory output mechanism 190 of an exercise bar 100 has been described in accordance with various embodiments of the present disclosure, a method for displaying exercise information is provided in accordance with various embodiments of the present disclosure.

Referring to FIG. 12, an exemplary method 1200 for displaying exercise information is provided, in accordance with some embodiments of the present disclosure. In the flow charts, the preferred parts of the methods are shown in solid line boxes, whereas optional variants of the methods, or optional equipment used by the methods, are shown in dashed line boxes.

Various modules in the in the memory 292 of the exercise bar 100, the memory 392 of the exercise system 200, the memory 492 of a client device 300, or a combination thereof perform certain processes of the methods 1200 described in FIG. 12, unless expressly stated otherwise. Furthermore, it will be appreciated that the processes in FIG. 12 can be encoded in a single module or any combination of modules.

Block 1202. Referring to block 1202 of FIG. 12, a method 1200 is provided for displaying exercise data at a computer system (e.g., exercise system 200 of FIG. 3, client device 300 of FIG. 4, etc.). The computer system includes a display (e.g., display 378 of FIG. 4), one or more processors (e.g., CPU 372 of FIG. 4), and a memory (e.g., memory 392 of FIG. 4). The memory stores at least one program for execution by the one or more processors. The at least one program includes instructions performing the method 1200.

Block 1204. Referring to block 1204, the method 1100 includes receiving, in electronic format, from an exercise bar 100, a plurality of data elements. In some embodiments, the plurality of data elements is captured, at least in part, when a user is performing an exercise that causes an offsetting a longitudinal axis of the exercise bar 100. For instance, in some embodiments, the plurality of data elements is captured by a sensor 180 housed by the exercise bar 100 when the user is performing the exercise that causes the offsetting the longitudinal axis of the exercise bar 100 during a first continuous period of time and, optionally, processed by the processor 272 of the exercise bar 100. In some embodiments, the plurality of data elements is captured by a sensor 180 housed by the exercise bar 100 when the user is performing the exercise that causes the offsetting the longitudinal axis of the exercise bar 100 during a first discontinuous period of time (e.g., multiple exercise sessions with rest in between two or more sessions) and, optionally, processed by the processor 272 of the exercise bar 100.

In some embodiments, the plurality of data elements includes a first set of data elements associated with a strain of the exercise bar 100 when offsetting of the longitudinal axis of the exercise bar 100. For instance, in some embodiments, the first set of data elements associated with a strain of the exercise bar 100 includes a maximum elongation of the exercise bar 100, a minimum elongation of the exercise bar 100, an intermittent elongation of the exercise bar, or any combination thereof.

In some embodiments, the strain ($\varepsilon$) is defined as a function of a change in a gauge length ($\delta$) against an original gauge length (L), such as: $\varepsilon = \delta/L$. For instance, in some embodiments, a strain of X % means a change in length of the exercise bar 100 as a function of an original length of the exercise bar 100, where X is a number between 0 and 100. In some embodiments, the strain of X % means a change in diameter of the exercise bar 102 as a function of an original diameter of the exercise bar, such as a change between a first original diameter of the exercise bar prior to the offsetting of the exercise bar and a second diameter of the exercise bar during the offsetting of the exercise bar. As a non-limiting example, if an original length of the exercise bar is 100 cm and the exercise bar is subjected to 1% strain to elongate to a new length of 101 cm. However, the present disclosure is not limited thereto.

In some embodiments, the offsetting includes a vertical displacement of the longitudinal axis of the exercise bar 100, such by performing a squat exercise 214 or a bench press exercise 214 with the exercise bar 100. In some embodiments, the vertical displacement is away from the ground and/or towards the ground. In some embodiments, by providing the vertical displacement of the exercise bar 100, the user exerts energy (e.g., work) on the exercise bar that generates strain, which is represented through the data elements generated by the exercise bar, providing improved workouts for the user.

Block 1206. Referring to block 1206, the method 1100 includes generating, by one or more models, from a set of data elements in the plurality of data elements, a digital representation of the set of data elements (e.g., user interface 1500 of FIG. 15, user interface 1600 of FIG. 16, user interface 1700 of FIG. 17, user interface 1800 of FIG. 18, etc.). In some embodiments, the digital representation is generated remote from the exercise bar 100. However, the present disclosure is not limited thereto.

In some embodiments, the method 1100 of FIG. 11 and/or the method 1200 of FIG. 12 is performed with one or more models 222 of a client device 300 and/or an exercise system 200. For instance, in some embodiments, a first model is configured to acquire a corresponding value for each threshold condition in the first plurality of threshold conditions, a second model is configured to fire the plurality of light source sets, and a third model is configured to determine if a corresponding value for each threshold condition is satisfied. By using the plurality of classifies, the systems and methods of the present disclosure provide for a more robust firing of the plurality of light source sets, while ensuring the safety of a subject nearby. In some embodiments, each respective model produces a result in the plurality of model results that identifies a respective node of the plurality of nodes that best matches with a subset of data elements with a corresponding determination in a plurality of determinations in accordance with a corresponding model in the plurality of models. Said otherwise, in some embodiments, the model is implemented as an artificial intelligence engine. For instance, in some embodiments, the model includes one or more gradient boosting model, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set) that includes one or more features identified from a data set. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using a priori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as minimum cut, harmonic function, manifold regularization, etc.), heuristic approaches, or support vector machines. In some embodiments, the supervision of a respective model is performed by an administrator associated with an entity that utilizes the systems and methods of the present disclosure.

NNs include conditional random fields, convolutional neural networks, attention based neural networks, deep learning, long short term memory networks, or other neural models.

While MLA and neural networks identify distinct approaches to machine learning, the terms may be used interchangeably herein. Thus, a mention of MLA may include a corresponding NN or a mention of NN may include a corresponding MLA unless explicitly stated otherwise. In some embodiments, the training of a respective model includes providing one or more optimized datasets, labeling these features as they occur (e.g., in user profile 16 records), and training the MLA to predict or classify based on new inputs, such as based on data captured when firing the plurality of light source sets 110. Artificial NNs are efficient computing models which have shown their strengths in solving hard problems in artificial intelligence. For instance, artificial NNs have also been shown to be universal approximators, that is, they can represent a wide variety of functions when given appropriate parameters.

Accordingly, in some embodiments, a first model is a neural network classification model, a second model is a Naïve Bayes classification model, and the like. Furthermore, in some embodiments, the model includes decision tree algorithm, a neural network algorithm, a support vector machine (SVM) algorithm, and the like. Moreover, in some embodiments, the classifier used in the (e.g., method 3400 of FIG. 34, etc.) described herein is a logistic regression algorithm, a neural network algorithm, a convolutional neural network algorithm, a support vector machine (SVM) algorithm, a Naïve Bayes algorithm, a nearest neighbor algorithm, a boosted trees algorithm, a random forest algorithm, a decision tree algorithm, a clustering algorithm, or a combination thereof.

One of skill in the art will readily appreciate other models that are applicable to the systems and methods of the present disclosure. In some embodiments, the systems and methods of the present disclosure utilize more than one model to provide an evaluation (e.g., arrive at an evaluation given one or more inputs) with an increased accuracy. For instance, in some embodiments, each respective model arrives at a corresponding determination when provided a respective data set. Accordingly, each respective model can independently arrive and a result and then the result of each respective model is collectively verified through a comparison or amalgamation of the models. From this, a cumulative result is provided by the models. However, the present disclosure is not limited thereto.

In some embodiments, a respective model is tasked with performing a corresponding activity (e.g., block 1104 of method 1100 of FIG. 11, block 1108 of method 1100 of FIG. 11, block 1110 of method 1100 of FIG. 11, block 1204 of method 1200 of FIG. 12, block 1206 of method 1200 of FIG. 12, block 1208 of method 1200 of FIG. 12, block 1210 of method 1200 of FIG. 12, block 1212 of method 1200 of FIG. 12, etc.). In some embodiments, each respective model of the present disclosure makes use of 10 or more parameters, 100 or more parameters, 1000 or more parameters, 10,000 or more parameters, or 100,000 or more parameters. In some embodiments, each respective model of the present disclosure makes use of 10 or more parameters, 100 or more parameters, 1000 or more parameters, 10,000 or more parameters, or 100,000 or more parameters. In some embodiments, each respective model 224 of the present disclosure cannot be mentally performed.

In some embodiments, the plurality of models 224 includes six or more models 224. In some embodiments, each model 224 in the plurality of models 224 is independently selected from the group consisting of: Naïve Bayes, decision tree, logistic regression, support vector machine, random forest, and artificial neural network. In some embodiments, a model 224 in the plurality of models 224 is a support vector machine, a clustering algorithm, a neural network, a decision tree, a logistic regression, a linear regression module, or a k-nearest neighbor model.

In some embodiments, the digital representation represents the vertical displacement of the longitudinal axis of the exercise bar 100. In some embodiments, the digital representation represents the vertical displacement of the longitudinal axis in substantially real-time, such as by displaying information representing the vertical displacement of the exercise bar (e.g., a strain, a height, etc.) within between 0.01 seconds and 2 seconds, between 0.1 seconds and 1 second, or within between 0.3 seconds and 0.5 seconds of when the exercise bar is displaced. In some embodiments, the digital representation includes a table, a chart, a graph, or a combination thereof (e.g., user interface 1500 of FIG. 15, user interface 1600 of FIG. 16, user interface 1700 of FIG. 17, user interface 1800 of FIG. 18, etc.). In some embodiments, the digital representation represents a maximum strain when offsetting of the longitudinal axis of the exercise bar. In some embodiments, the digital representation represents a period of time associated with the offsetting of the longitudinal axis of the exercise bar, such as a period of time that includes when the exercise bar is at rest, a point in time when the exercise bar transitions from rest to movement, a point in time when the exercise bar transitions from movement to rest, or a combination thereof.

In some embodiments, the period of time includes a first period of time of the offsetting of the longitudinal axis during the receiving the plurality of data elements that is associated with a phase of the offsetting of the longitudinal axis during the receiving the plurality of data elements or an average period of time associated with the phase of the offsetting of the longitudinal axis during the receiving the plurality of data elements. For instance, in some embodiments, the period of time is associated with a repetition (e.g., rep) of an exercise performed with the exercise bar by the user.

In some embodiments, the phase of the offsetting of the offsetting of the longitudinal axis during the receiving the plurality of data elements is an eccentric phase of an exercise performed with the exercise bar by the user, a concentric phase of the exercise performed with the exercise bar by the user, an isometric phase of the exercise performed with the exercise bar by the user, or a combination thereof. However, the present disclosure is not limited thereto.

In some embodiments, the generating the digital representation further includes generating, by the one or more models 224, the digital representation from: the set of data elements; a historical set of data elements from a previous instance of the receiving of the plurality of data elements, the generating the digital representation, and the displaying the digital representation; a resistance applied to the exercise bar; a type of exercise performed by a user of the exercise bar when performing the method 1200 and/or the method 1100, or a combination thereof. However, the present disclosure is not limited thereto.

In some embodiments, the generating the digital representation further includes evaluating, by the one or more models 224, the set of data elements, and, in accordance with a determination that each threshold condition in a first set of threshold conditions, in a plurality of threshold conditions, is satisfied, generating one or more instructions for firing a first configuration of a sensory output mechanism of the exercise bar. However, the present disclosure is not limited thereto.

In some embodiments, the method 1200 further includes communicating, in electronic format, the one or more instructions for firing the first configuration to the exercise bar 100. In some embodiments, this communicating the one or more instructions is facilitated through the communication network 106, which allows for remote firing of the first configuration of the exercise bar 100. However, the present disclosure is not limited thereto.

In some embodiments, the sensory output mechanism 190 of the exercise bar includes 190, one or more light source output mechanisms 190, one or more vibration output mechanisms 190, one or more audio output mechanisms 190, or a combination thereof.

Block 1208. Referring to block 1108, the method 1100 includes displaying, on the display 378 of the client device 300, the digital representation of the set of data elements. In some embodiments, this displaying the digital representation of the set of data elements occurs dynamically in accordance with the generating of the digital representation, which allows the user to view the exercise information in real time as the user performs a respective exercise 214 with the exercise bar 100.

In some embodiments, the set of data elements is selected from the plurality of data elements by the one or more models (e.g., first models 224-1 and/or model V 224-V of FIG. 2B). In some embodiments, the one or more models 224 select the set of data elements based on a selection by the user for the digital representation. For instance, in some embodiments, the selection by the user for the digital representation is a selection for a first digital representation of the vertical displace of the exercise bar 100, the amount of the strain measured by the sensor 180 when offsetting the longitudinal axis of the exercise bar 100, the period of time of a phase of the offsetting of the exercise bar 100 (e.g., an eccentric phase, a concentric phase, an isometric phase, etc.), or a combination thereof. In this way, in some embodiments, the one or more models 224 select the best fit data elements as the set of data elements as the basis of the digital representation.

In some embodiments, the display of the digital representation includes a chart. The chart includes a plurality of nodes (e.g., nodes 1010 of FIG. 17). Furthermore, the chart includes at least one edge (e.g., edge 1020 of FIG. 17) that is configured to connecting a respective node in the plurality of nodes to at least one other node. In some embodiments, the at least one edge is visible when the display of the digital representation is provided to the user (e.g., digital representation 1000 of FIG. 16). However, the present disclosure is not limited thereto. In some embodiments, the chart includes one or more axis that define a boundary for placement of the plurality of nodes 1010 and the at least one edge within the chart 100. For instance, referring briefly to FIG. 16, a horizontal axis defines a period of time associated with the digital representation (e.g., period of time when the user is performing the exercise 214). However, the present disclosure is not limited thereto. In some embodiments, each respective node 1010 in the plurality of nodes 1010 represents a corresponding data element in the set of data elements. For instance, in some embodiments, the corresponding data element represented by the respective node is associated with a vertical displacement of the longitudinal axis of the exercise bar. Furthermore, in some embodiments, the corresponding data element represented by the respective node is associated with the vertical displacement of the longitudinal axis at a point in time. Moreover, in some embodiments, the corresponding data element represented by the respective node is associated with a maximum strain when offsetting of the longitudinal axis of the exercise bar. In some embodiments, the corresponding data element represented by the respective node is associated with a period of time Block 1210. Referring to block 1210, in some embodiments, the method 1100 further includes repeating the receiving the plurality of data elements, the generating the digital representation, and the displaying the digital representation. From this, the digital representation is dynamically updated responsive to this repeating. Accordingly, this allows the user to view the displayed digital representation when performing an exercise 214 with the exercise bar 100 and having the digital representation update in real time based on how the user is performing the exercise 214, such as by showing an instant height of the exercise bar or strain measured by the sensor 180.

Block 1212. Referring to block 1212, in some embodiments, the method 1200 includes communicating, in electronic format, the one or more instructions for firing the first configuration to the exercise bar 100. For instance, in some embodiments, responsive to a step of method 1200 (e.g., block 1204, block 1204, block 1208, block 1210, or a combination thereof), the communicating the one or more instructions causes a controller of the exercise bar 100 to change a respective state of a sensory output mechanism 190 of the exercise bar, such as based on the determined amount of the strain applied to the exercise bar 100. In this way, the one or more instructions cause the user operating the exercise bar 100 to sense the change in the respective state of the sensory output mechanism (e.g., method 1200). However, the present disclosure is not limited thereto.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. For instance, the computer program product could contain instructions for operating the user interfaces disclosed herein and described with respect to FIGS. 2A, 2B, 3, 4, 11, 12, 13, 14, 15, 16, 17, and 18. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. An exercise bar comprising:
   a handle tube with a longitudinal interior bore, the handle tube having a first end and a second end;
   a center shaft having an outer surface, wherein the center shaft is fitted through the longitudinal interior bore thereby exposing a first end portion of the center shaft at the first end of the handle tube and exposing a second end portion of the center shaft at the second end of the handle tube, and wherein the center shaft longitudinally rotates independent of the handle tube while coupled with the handle tube;
   a sensor disposed on a mounting section of the outer surface of the center shaft between the first end portion and the second end portion of the center shaft wherein the mounting section is at a midpoint of the center shaft; and
   a processor disposed in an interior of the exercise bar, wherein the sensor is in electronic communication with the processor in the exercise bar.

2. The exercise bar of claim 1, wherein the center shaft is a hollow center shaft.

3. The exercise bar of claim 2, wherein the mounting section comprises a lateral bore, thereby exposing an interior of the hollow center shaft for physical electronic communication between the sensor and the processor.

4. The exercise bar of claim 3, wherein the exercise bar further comprises a switch mechanism interposing between the sensor and the processor, the switch mechanism configured to interrupt the electronic communication.

5. The exercise bar of claim 1, wherein the sensor comprises a strain sensor.

6. The exercise bar of claim 1, wherein the sensor comprises a Wheatstone bridge sensor.

7. The exercise bar of claim 6, wherein the Wheatstone bridge sensor is a balanced Wheatstone bridge sensor.

8. The exercise bar of claim 6, wherein the Wheatstone bridge sensor is a full Wheatstone bridge sensor.

9. The exercise bar of claim 1, wherein the exercise bar further comprises a first end cap fixedly disposed about the first end of the handle tube or the first end portion of the center shaft.

10. The exercise bar of claim 9, wherein the first end cap is fixedly disposed about the first end portion of the center shaft, and wherein the first end cap longitudinally rotates independent of the handle tube.

11. The exercise bar of claim 9, further comprising a second end cap fixedly disposed about the second end of the handle tube or the second end portion of the center shaft.

12. The exercise bar of claim 11, wherein the second end cap is configured to accommodate a battery configured to provide power to at least the processor.

13. The exercise bar of claim 12, wherein an exterior circumferential surface of the first end cap comprises a first bore configured to accommodate a light source in electronic communication with the processor.

14. The exercise bar of claim 1, wherein an exterior circumferential surface of the handle tube further comprises a first bore configured to accommodate a light source in electronic communication with the processor.

15. The exercise bar of claim 14, wherein a first end portion of the first bore comprises an aperture configured to accommodate the light source, thereby exposing an interior of the first bore.

16. The exercise bar of claim 1, wherein the mounting section comprises a portion of the outer surface of the center shaft that is flat and has spatial dimensions that are configured to accommodate the sensor.

17. The exercise bar of claim 16, wherein the portion of the mounting section is recessed into the center shaft by a first depth.

18. The exercise bar of claim 1, wherein the processor is an integrated circuit comprising a transceiver.

* * * * *